United States Patent
Gao et al.

(10) Patent No.: US 7,030,257 B2
(45) Date of Patent: Apr. 18, 2006

(54) METALLOCENES AND PROCESSES FOR THEIR PREPARATION

(75) Inventors: Zhiqiang Gao, Choa Chu Kang Crescent (SG); Fang Xie, West Coast Crescent (SG); Hong Xie, Choe Chu Kang Central (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 10/823,169

(22) Filed: Apr. 13, 2004

(65) Prior Publication Data

US 2005/0228189 A1 Oct. 13, 2005

(51) Int. Cl.
*C07F 17/02* (2006.01)
*B01J 31/00* (2006.01)
*C12Q 1/68* (2006.01)
*C07C 291/00* (2006.01)

(52) U.S. Cl. .................. 556/140; 556/47; 556/53; 556/58; 556/136; 502/155; 435/6; 564/298

(58) Field of Classification Search .................. 556/47, 556/53, 58, 136, 140; 502/155; 564/298; 435/6

See application file for complete search history.

(56) References Cited

FOREIGN PATENT DOCUMENTS

GB 767298 0/1957
GB 896391 0/1962

OTHER PUBLICATIONS

Younkin et al., "Neutral, Single-Component Nickel (II) Polyolefin Catalysts That Tolerate Heteroatoms", Science, 287:460-462, (2000).
Togni et al., "Vol. 1, Synthesis and Reactivity", Metallocenes, Chapter 1; Wiley, NY (1998).
Togni et al., "vol. 2, Applications", Metallocenes, Chapter 11, Wiley, NY (1998).
Que Jr. et al., "Dioxygen Activation by Enzymes with Mononuclear Non-Heme Iron Active Sites", Chem Rev., 96:2607-2624, (1996).
Wallar et al., "Dioxygen Activation by Enzymes Containing Binuclear Non-Heme Iron Clusters", Chem Rev., 96:2625-2657, (1996).
Kappock et al., "Pterin-Dependent Amino Acid Hydroxylases", Chem Rev., 96:2659-2756, (1996).
Sono et al., "Heme-Containing Oxygenases", Chem Rev., 96:2841-2887, (1996).
Sharp et al., Electrochemistry in Liquid Sulfur Dioxide. 4. Electrochemical Production of Highly Oxidized Forms of Ferrocene, Decamethylferrocene, and Iron Bis(tris(1-pyrazolyl)borate); Inorg. Chem. vol. 22:2689-2693, (1983).

(Continued)

*Primary Examiner*—Porfirio Nazario-Gonzalez
(74) *Attorney, Agent, or Firm*—Stout, Uxa, Buyan & Mullins, LLP; Greg S. Hollrigel

(57) ABSTRACT

Disclosed herein are novel high oxidation state metallocene compounds, processes for preparing these compounds and uses of these compounds.

19 Claims, 14 Drawing Sheets

OTHER PUBLICATIONS

Gale et al., "Metallocene Electrochemistry I. Evidence for Electronic Stabilization with Alkylated Cyclopentadiene: Electrochemical Synthesis of DecaMethylferricinium Dication", J. of Organometallic Chemistry 199:C44-C46, (1980).

Wilson et al., "The Existence of the Nickel (IV) Dication Derived from Nickelocene and a Cationic Boron Hydride Analog", J. of American Chem. Society, 91:3:758-759 (Jan. 29, 1969).

Kuwana et al., "Chronopotentiometric Studies on the Oxidation of Ferrocene, Ruthenocene, Osmocene and Some of their Derivatives", J. Am. Chem. Soc. 82:5811-5817, (1960).

March & Smith, "Transmetalation with Metal Halide", Advanced Organic Chemistry, 5th ed., Wiley-InterScience, 803-804.

Fukuzawa, "Optically Active 1,2-Bis(1-arylhydroxymethyl) Ferrocene: A new, efficient chiral ligand of scandium-catalyzed asymmetric diels-alder reaction", Organic Letters 4:707-709 (2002).

Nicolosi et al., "Lipase mediated desymmetrization of 1,2-Bis(hydroxymethyl)ferrocene in Organic Medium: Production of Both Enantiomers of 2-Acetoxymethyl-1-hydroxymethylferrocene", Tetrahedron: Assymetry 3:753-758 (1992).

Vos et al., "Synthesis of Tetra-3-butenyl-Substituted Metallocenes and the Application of 1,1',3,3'-Tetrakis(1,1-dimethyl-3-butenyl)ferrocene as Core for the preparation of polynuclear compounds", Organometallics 19:3874-3878 (2000).

Broussier et al., "New 1,1'-or 1,2- or 1,3-bis (diphenylphosphino)ferrocenes", J. Organometallic Chem. 598:365-373 (2000).

March & Smith, Advanced Organic Chemistry, 5th ed. Wiley-InterScience, 1056-1057.

Yu et al., "Synthesis, characterization and in vitro antitumor activity of some arylantimony ferrocenylcarboxylate derivatives and the crystal structures of $[C_5H_5FeC_5H_4C(CH_3)=CHCOO]_2Sb(C_6H_4F-4)_3$ and $[4-(C_5H_5FeC_5H_4)C_8H_4COO]_2Sb(C_8H_4F-4)_3$", Polyhedron, 23:823-829 (2004).

Kovjazin et al., "Ferrocene-induced lymphocyte activation and antitumor activity is mediated by redox-sensitive signaling", The FASEB Journal, 10.1096/fj.02-0558fje (2003).

Tabbi et al., Water Stability and Cytotoxity Activity Relationship of a Series of Ferrocenium Derivatives. ESR Insights on the Radical Production during the Degradation Process., J. Med. Chem. 45:5786-5796 (2002).

Osella et al., "On the mechanism of the antitumor activity of ferrocenium derivatives" Inorganica Chimica Acta. 306:42-48 (2000).

Houlton et al., "Studies on the anti-tumour activity of some iron sandwich compounds", J. Organometallic Chemistry, 418:107-112 (1991).

English translation of Frohlich et al., "Insertion and reductive coupling of carbin dioxide; in the formation of $Cp_2Ti^{III}C_2O_4Ti^{III}CP_2$ and $Cp_2Ti^{IV}$ $[-O_2C(CH_2)_2NRCH_2CH_2NR(CH_2)_3CO_2-]$ $(R=iso-C_4H_9)$"; Zeitschrift fur Chemie; 1983: 23(9), 348-349.

English translation of Schreer et al., "Synthesis of metallacyclic titanium compounds of the types $Cp_2TI(CH_2)_3NRC_2H_4RN(CH_2)sTiCp_2$ and $Cp_2Ti(CH_2)_3NRR$"; Chemie; 1983; 23(9), 347-348.

STN File CA Abstract Accession No. 100:103535; Schreer et al., "Synthesis of metallacyclic titanium compounds", Zeitschrift fur Chemie (1983), 23(9), 347-8. And, English translation of Abstract.

International Search Report mailed May 12, 2005 for International Application No. PCT/SG2005/000120, filed Apr. 12, 2005.

STN File CA Abstract Accession No. 100:156736; Frolich et al., "Insertion and reductive coupling of carbon dioxide; formation of $Cp_2Ti^{III}C_2O_4Ti^{III}Cp_2$ and $Cp_2Ti^{IV}[-O_2C(CH_2)_3NRCH_2CH_2NR-(CH_2)_3CO_2-]$ $(R=iso-C_4H_9)$", Zeitschrift fur Chemie (1983), 23(9), 348-9. And, English translation of Abstract.

METALLOCENES AND PROCESSES FOR THEIR PREPARATION

This invention relates to novel metallocene compounds, in particular high oxidation state metallocene compounds, as well as processes for preparing these compounds and uses thereof.

BACKGROUND OF THE INVENTION

Since the discovery and elucidation of the structure of ferrocene in the early 1950s, metallocenes of transition metals such as iron, niobium, vanadium, tungsten, chromium, nickel, cobalt, manganese or ruthenium have been a continual source of intrigue for chemists and material scientists.

One traditional application of metallocenes was their used as catalysts in olefin polymerisation; reviewed, for example, by Younkin et al., Science, (2000) Vol. 287, pages 460–462 who also report recent developments of biscyclopentadienyl and monocylcopentadienyl metallocenes of "early" transition metal that are used as homogenous polymerisation catalysts.

As methods for producing more stable and active metallocenes were developed over the years, their use have expanded to other areas of application in which their electrochemistry had an important role, such as electronic applications including molecular switches, metal probes, molecular magnets, non-linear optics and, more commonly, as a mediator in enzyme electrodes.

Metallocenes such as ferrocenes are also currently undergoing a renaissance due to their increasing role in the rapidly growing area of material sciences. For example, ferrocene-containing materials have found widespread applications not only in catalysis but also biosensing, thermotrophic liquid crystals and non-linear optics (cf. A. Author, in Metallocenes. Synthesis Reactivity, Applications, Vol. 1, Chapter 1; Vol. 2, Chapter 11; A. Togni and R. L Halterman, Eds, Wiley, New York, 1998).

Iron in high oxidation states such as Fe(III) and Fe(IV) has also been found to be involved in biological processes. For example, a wide range of heme and non-heme iron-containing oxygenase enzymes were found to be involved in the mediation of oxygen atom transfer in biological systems. Additionally, dioxygen activation by metalloenzymes and biomimetic complexes has fuelled interest in high-valent metal complexes as models for biocatalysis. (cf. Chem. Rev. 96(1996) 2607–2624, 2625–265, 2659–2756, 2841–2887)

Due to their stability, ferrocene compounds are however typically based on the ferrocenium ion (Fc$^+$) in which the iron atom is present as Fe (III), whereas the (Fc$^{2+}$) species in which the iron is present in oxidation state (IV) have not been isolated because the stability of Fc$^{2+}$ decreases significantly. The existence of such ferrocene derivatives was confirmed only electrochemically under the stringent conditions (in liquid $SO_2$, $-40°$ C. by Sharp & Bard (Inorg. Chem. Vol. 22, No. 19, 1983) or Gale et al (J. Organom. Chem. 199 (1980) C44–C46)

A similar instability was reported for other high oxidation state metallocenes earlier. For example, Wilson et al. (JACS 91, 758, (1969)) achieved the reversible oxidation of nickel from the oxidation state of (III) to (IV) in nickelocene using cyclic voltammetry in acetonitrile solution. However, it was necessary to use a process temperature of $-40°$ C. in order to prevent the nickel (IV) species from rapidly decomposing. Likewise, Kuwana et al. (JACS, 82, 5811 (1960)) described a one-step, two electron oxidation of ruthenocene. In inert medium and at ambient temperature, the obtained ruthenocene dipositive ion decomposed over a period of about 10 hours.

Accordingly, there remains a need for stable metal complexes which can be used, either as model compounds or directly in practical applications, in the above mentioned areas such as biocatalysis or biosensing.

SUMMARY OF THE INVENTION

In one aspect, the present invention provides a compound having the formula (I):

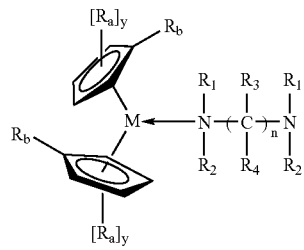

wherein:

M is a transition metal selected from Groups 4 to 10 (IUPAC, 1990);

$R_a$ is H or C1 to C6 alkyl, optionally substituted;

y is an integer of 1 or 2;

$R_b$ is H or a vinyl group having the formula (II):

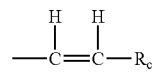

or the formula (IIA):

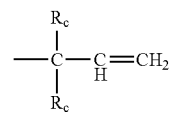

or the formula (IIB):

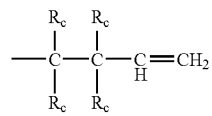

wherein $R_c$ is H or C1 to C6 alkyl, optionally substituted;

$R_1$ and $R_2$ are independently selected from C1 to C6 alkyl, optionally substituted;

$R_3$ and $R_4$ are independently selected from H or C1 to C6 alkyl, optionally substituted; and n is an integer of 2 or 3.

Another aspect of the invention is directed to a process for preparing an organometallic compound comprising:

reacting a compound having the formula (III):

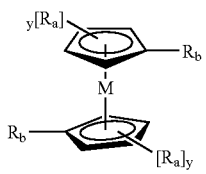

with a compound having the formula (IV):

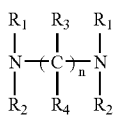

wherein:
M is a transition metal selected from Groups 4 to 10 (IUPAC, 1990);
$R_a$ is H or C1 to C6 alkyl, optionally substituted;
y is an integer of 1 or 2;
$R_b$ is H or a vinyl group having the formula (II):

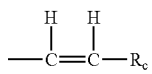

or the formula (IIA):

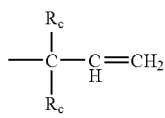

or the formula (IIB):

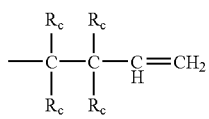

wherein $R_c$ is H or C1 to C6 alkyl, optionally substituted;
$R_1$ and $R_2$ are independently C1 to C6 alkyl, optionally substituted,
$R_3$ and $R_4$ are independently H or $CH_3$, optionally substituted; and
n is an integer of 2 or 3;
said reaction being carried out in the presence of an oxidising agent.

A further aspect of the invention is directed to various uses of compounds of the present invention, for example, as a nucleic acid intercalating agent or as a catalyst for the oxidation of amines.

BRIEF DESCRIPTION OF THE DRAWINGS

The invention will be better understood with reference to the detailed description when considered in conjunction with the non-limiting examples and the drawings, in which:

FIGS. 1C and 1D show VFcTMEDA and VFcTMPDA in which the diamine portion is depicted as being bound to the metallocene portion as a bidentate ligand.

DETAILED DESCRIPTION

Figure 1A:
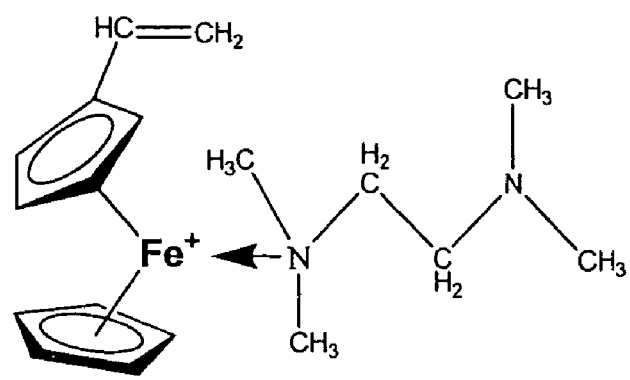
FIGS. 1A and 1B show examples of the water-soluble, high oxidation state compound of the present invention, namely vinylferrocene tetramethylethylenediamine (hereinafter referred to as 'VFcTMEDA') and vinylferrocene tetramethylpropylenediamine (hereinafter referred to as 'VFcTMPDA). In these figures, the diamine portion is depicted as being bound to the metallocene portion as a monodentate ligand.

In one aspect, the present invention is based on the surprising finding that stable high oxidation state metallocene compounds are obtainable for the first time by reacting a metallocene with tertiary amines in the presence of an oxidising agent. In the past, due to problems in stability, high oxidation state metallocene compounds were not readily available. The present invention thus provides a method for obtaining stable high oxidation state metallocenes that can be carried out, stored and used even at ambient conditions. Accordingly, the present invention also provides new metallocene compounds with useful properties that can be harnessed in many applications.

As can be taken from formula (I), the compounds of the present invention are complexes comprising a metallocene portion and a diamine portion.

In the metallocene portion, M is any suitable transition metal from Groups 4 to 10 (IUPAC, 1990). M can be present in the compound either as a charged cation or an uncharged species. Preferred transition metals are selected from Fe, Co, Ni, Mn, Cr, Zr, Ti, V, Os and Ru. Accordingly, the metallocene portion of the compound of formula (I) can be derived from, far example, ferrocene, cobaltacene, nickelocene, manganocene, chromocene, zirconocene, titanocene, vanadocene, osmocene and ruthenocene. The partially filled d or f shells in these metals make it possible for metallocenes to attain reversible oxidation states, and thus the ability to form coordinate bonds with suitable ligands. Particularly suitable transition metals are those that are able to attain oxidation states of +1, +2, +3, +4 or +5, so as to form coordinative bonds with suitable ligands.

The two ligands that are coordinatively bonded to M in the metallocene are each (based on) a cyclopentadienyl ring (hereinafter referred to as 'Cp'). Each Cp ring contains the substituents $R_a$ and $R_b$.

As defined in formula (I), $R_a$ can be a hydrogen atom (i.e. the ring carbon atom to which $R_a$ is attached is unsubstituted) or an alkyl group comprising 1 to 6 main chain carbon atoms. $R_a$ may be thus straight chained or branched, and each $R_a$ may also be optionally substituted. Examples of substitutions of $R_a$ are aromatic groups such as phenyl and benzyl, —$NO_2$, —$NH_2$, —NHR, wherein R is an alkyl group, —COOH, —CN, —OH, —$SO_3H$, or halogen. Each Cp ring can have one or two $R_a$ substituents bonded to any ring carbon atom on the Cp ring. For example, where one $R_a$ substituent is present in each Cp ring, it may be present at either the α or the β position with respect to the substituent $R_b$. In one embodiment, $R_a$ is present at the α position, meaning that the Cp ring is a 1,2-disubstituted ring. In this embodiment, the compound of the invention has the structure according to formula (IA):

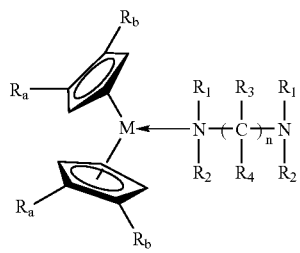

wherein M, $R_a$, $R_b$, $R_1$, $R_2$, $R_3$ and $R_4$ have the same meanings as defined above.

In another embodiment in which one $R_a$ substituent is present in each Cp ring, $R_a$ is present at the β position, meaning that each Cp ring is a 1,3-disubstituted ring. In this embodiment, the compound of the invention has the structure according to formula (IB):

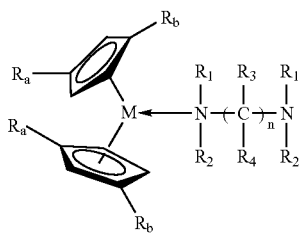

wherein M, $R_a$, $R_b$, $R_1$, $R_2$, $R_3$ and $R_4$ have the same meanings as defined above.

In case two $R_a$ substituents are present, each $R_a$ substituent may be present at the α position with respect to the substituent $R_b$, resulting in a 1,2,5-trisubstituted Cp ring. Alternatively, one $R_a$ substituent is located at the α position and the other $R_a$ substituent is located at the β position with respect to the substituent $R_b$, resulting in a 1,2,4-trisubstituted Cp ring. 1,2,3-trisubstituted and 1,3,4-trisubstituted Cp rings moieties can also be used in the compound of the invention.

The substituent $R_b$ is a hydrogen atom or a vinyl side group having the formula (II):

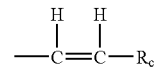

This vinyl radical may be substituted or unsubstituted at the side group $R_c$. Both cis and trans isomers of the vinyl group with respect to the metallocene and $R_c$ moieties may be present in the compound of formula (I). Alternatively, $R_b$ can have the structure according to formula (IIA):

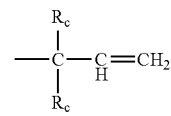

or the formula (IIB):

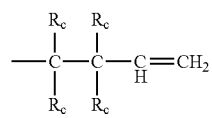

Rc is either a hydrogen atom, or a C1 to C6 alkyl group, each of which may be optionally substituted.

In one embodiment, the moieties $R_a$ and $R_c$ as defined in formula (I) are each independently selected from the group consisting of hydrogen atom, methyl, ethyl, propyl, iso-propyl, butyl, n-butyl, tert-butyl, pentyl, n-pentyl, iso-pentyl, n-hexyl, iso-hexyl. The hydrogen atoms of each carbon atom of alkyl groups can be optionally substituted. Each of these alkyl substituents can be of any suitable structure, including straight chained or branched structures.

Each $R_a$ present in the compound of formula (I) is independently selected. This means that a Cp ring in the compound can have, for example, 2 different $R_a$. In addition, $R_b$ of each ring are also independently selected. This means that $R_a$ and $R_b$ of one ring can be the same as or different from the $R_a$ and $R_b$ of another ring in formula (I). Where the substituents of one ring are different from the substituents of the other ring, this means that one ring can be, for example, a vinyl cyclopentadiene while the other ring can be an unsubstituted cyclopentadiene, thus being an asymmetrical compound 1-vinyl-metallocene for example. Where both rings have identical substituents, e.g. both rings are vinyl-cyclopentadiene, the compound is symmetrical, for example 1,1'-bis-vinylferrocene.

In the context of the present invention, optionally substituted carbon atoms refer to carbon atoms wherein hydrogen atoms bonded thereto are replaced by one or more radicals, such as, but not restricted to aromatic residues such as phenyl, naphthyl, benzyl, —$NO_2$, —$NH_2$, —NHR wherein R is an alkyl group, —COOH, —CN, —OH, —$SO_3H$, or halogen. Halogen as used herein refers to chlorine, bromine, fluorine and iodine.

Specific examples of metallocenes that can be used to produce the compound of the present invention include, but are not limited to:

Ferrocene or ferrocene derivatives such as methylferrocene, ethylferrocene, propylferrocene, butylferrocene, tert-butylferrocene, 1,1'-dimethylferrocene, 1,1'-diethylferrocene, 1,1'-dipropylferrocene, vinylferrocene, 3-methylvinylferrocene, 3-ethylvinylferrocene, 3,3'-dimethyl-vinylferrocene, 3,3'-diethyl-vinylferrocene or 1,1'-Bis-vinylferrocene;

Cobaltocene or cobaltocene derivatives such as 1,1'-dimethylcobaltocene, 1,1'-diethylcobaltocene, 1,1'-bis(1-methylpropyl)cobaltocene, 1,1'-bis(1-methylethyl)cobaltocene, vinylcobaltocene or 3-methylvinylcobaltocene;

Nickelocene or nickelocene derivatives such as methylnickelocene, ethylnickelocene, propylnickelocene, 1,1'-dimethylnickelocene, vinylnickelocene or 3-methylvinylnickelocene;

Chromocene or chromocene derivatives such as 1,1'-dibutylchromocene, 1,1'-bis(1,1'-dimethylethyl)chromocene, 1,1'-diethylchromocene, vinylchromocene or 3-methyl-vinylchromocene;

Zirconocene or zirconocene derivatives such as methylzirconocene, 1,1'-diethylzirconocene, vinylzirconocene or 3-methyl-vinylchromocene;

Titanocenes or titanocene derivatives such as methyltitanocene, 1,1'-dimethyltitanocene, dibutyl-titanocene, vinyltitanocene or 3-methyltitanocene;

Vanadocene or vanadocene derivatives such as 1,1'-dimethylvanadocene, 1,1'-diethylvanadocene, 1,1'-dibutylvanadocene, vinylvanadocene or 3-methylvinylvanadocene;

Osmocene or osmocene derivatives such as 1,1'-dimethylosmocene, vinylosmocene or 3-methylvinylosmocene; or Ruthenocene or ruthenocene derivatives such as 1,1'-dimethylruthenocene, vinylruthenocene or 3-methylvinylruthenocene.

The compound of the invention can adopt any possible three dimensional structure. First, it is noted that the complex formed by the Cp ligands can assume a variety of rotational orientations. For example, the rings can be arranged in a staggered configuration or in an eclipsed configuration. In the eclipsed configuration, each carbon atoms in one ring lies on the same axis as each of the carbon atoms in the other ring. In the staggered configuration, each of the carbon atoms in the lie on a different axis from the carbon atoms in the other ring. One or both rotational configurations of the compound may be present in any sample of the compound. Additionally, the compound of the invention can have a straight or bent metallocene portion. When the angle that is formed between the two ligands and M about 180 degrees, the metallocene portion is 'straight'. It is also possible that the angle is less than 180 degrees such that a 'bent' configuration is obtained. Either configuration may be present in any sample of the compound of the invention. However, the quantities of each configuration may vary, depending on factors such as the steric effect presented by the different diamine portions.

As can be seen from formula (I), M is coordinatively bonded to the diamine portion, the bonds being represented by the arrow. The diamine portion has a structural according to formula (IV):

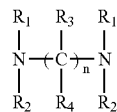

wherein n is the integer 2 or 3.

The diamine portion accordingly comprises two terminal tertiary amino groups. $R_1$ and $R_2$ in the diamine of formula (IV) are each, independently, C1 to C6 alkyl groups. Each carbon in the alkyl group may be optionally substituted, and the alkyl group may be straight chained or branched. In presently preferred embodiments, $R_1$ and $R_2$ are each independently selected from the group consisting of methyl, ethyl, n-propyl, iso-propyl, butyl, n-butyl, tert-butyl, pentyl, n-pentyl, iso-pentyl, n-hexyl, iso-hexyl.

In the compound of the invention, n is an integer of 2 or 3, meaning that the carbon chain in the diamine of formula (IV) is either a 2 carbon or 3 carbon chain. The substituents $R_3$ and $R_4$ are each independently selected from H or C1 to C6 alkyl. Where $R_3$ and $R_4$ are alkyl groups, they may be optionally substituted with one or more residues as defined above. They may be straight chained or branched. In other presently preferred embodiments, $R_3$ and $R_4$ are each independently selected from hydrogen, methyl, ethyl, propyl, iso-propyl, butyl, n-butyl, tert-butyl, pentyl, n-pentyl, iso-pentyl, n-hexyl, iso-hexyl.

Specific examples of diamines which are suitable as the diamine portion in formula (I) include but are not limited to: tetramethyl-1-methyl-ethylenediamine, tetraethyl-ethylenediamine, N,N'-diethyl-N,N'-dimethyl-ethylenediamine, N,N'-dimethyl-N,N'-diethyl-1-methyl-ethylenediamine, tetrapropyl-ethylenediamine, N,N'-dimethyl-N,N'-dipropyl-ethylenediamine, tetramethyl-propylenediamine, tetraethyl-2-ethyl-propylenediamine, N,N'-diethyl-N,N'-dimethyl-propylenediamine, and N,N'-Diisopropyl-N,N'-dimethyl-1,3-propanediamine.

Without wishing to be bound by theory, it is believed that the diamine bonded to M may act as a mono-dentate ligand in which only one of the nitrogen atoms donates a pair of unpaired electrons to form a coordinate bond with M as shown in the following formula (V) (in which the substituents of the Cp moiety are not shown for the sake of clarity) by way of example:

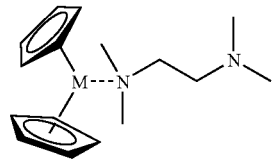

Alternatively, for instance, from the excellent nucleic acid intercalating properties of the compounds of the invention, as shown later, the possibility is also contemplated that this di-amino moiety is bonded to M as a bi-dentate ligand. When acting as a bidentate ligand, both nitrogen atoms of the two terminal amino groups should each contribute a pair of electrons to M to establish two coordinate bonds as shown in the following formula (VI) (in which the substituents of the Cp moiety are not shown for the sake of clarity) by way of example:

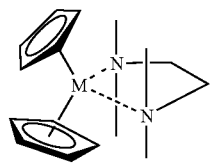

Therefore, the arrow used for the representation of the coordination of the diamine compound in formula (I) should not be construed to be limited to a specific coordination or stereochemistry but merely to illustrate that the amine is non-covalently bonded to the metal M.

In one embodiment, the overall charge of the compound of formula (I) is positive. Depending on the oxidation state of M, M as such can be uncharged or positively charged. Where the oxidation state of M balances the number of ligands attached to it, M is uncharged. However, it is possible, for example, by varying pH, temperature or the presence of an oxidising potential in a preparation process used that M can be oxidised to a higher oxidation state that is numerically larger than the number of ligands attached to it. In this case, M will be positively charged. In order to have a neutral compound, the positive charge can be neutralised by the presence of counter-ions that are negatively charged. The counter-ion can be provided during the synthesis of the compound, resulting in a salt of a compound of formula (I). Examples of counter-ions that are suitable in the invention include $SO_4^{2-}$, $Cl^-$, $Br^-$, $NO_3^-$, $H_2PO_4^-$, $HSO_4^-$, $PF_6^-$, $ClO_4^-$, $BF_4^-$, $F^-$, $I^-$, $CO_3^{2-}$, $HCO_3^-$, $NO_2^-$, $BrO_3^-$, $ClO_3^-$, $SiO_3^{2-}$, $CrO_4^{2-}$, $IO_4^-$, $SO_3^{2-}$, $HSO_3^-$ and $AsO_3^{2-}$.

Whilst any transition metal of the Groups 4 to 10 as defined in formula (I) can be used as the transition metal in the metallocene portion of the compound of the invention, Fe, Co, Ni, Mn, Cr, Zr, Ti, V, Os and Ru are preferred, as mentioned above. These metals are commonly used and have been studied in detail and are thus well characterised. In a preferred embodiment of the invention, the metallocene portion comprises a ferrocene, nickelocene or cobaltocene. In a further embodiment, a Cp ring carbon atom in the ferrocene, nickelocene or cobaltocene is substituted by a vinyl group, meaning that the metallocene portion is a vinylferrocene, vinylnickelocene or vinyl cobaltocene, respectively.

In one presently preferred embodiment, the compound of the invention has a structure according to formula (VII):

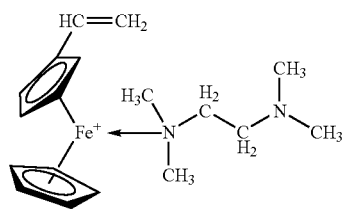

As shown in the above formula, this embodiment comprises a vinylferrocene portion and a tetramethylethylenediamine portion.

In another presently preferred embodiment, the compound of the invention has a structure according to formula (VII):

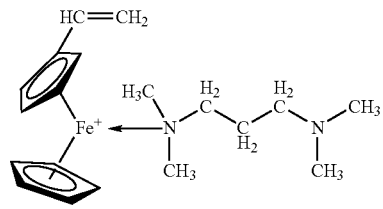

As shown in the above formula, this embodiment comprises a vinylferrocene portion and a tetramethylpropylenediamine portion.

Another aspect of the invention is directed to a process for preparing a compound as defined in formula (I). The process involves reacting a metallocene which corresponds to the structure of the metallocene portion of the desired compound as defined in formula (III), with a diamine that has a structure corresponding to the desired diamino portion of the compound as defined in formula (IV). In the present invention, the reaction may be typically carried out in the presence of an oxidising agent.

One advantage of the process of the invention, which may be a chemical synthesis or an electrochemical synthesis as explained below, is that it can be carried out efficiently at ambient room temperature and atmospheric pressure (i.e. "standard conditions"), unlike previously known processes which require cryogenic conditions, for example. On the other hand, depending on the exact reaction scheme used, in order to speed up the reaction, it is possible to carry out the reaction at an elevated temperature, for example, under reflux if a chemical synthesis is used. After the completion of the reaction, the product can be isolated from the reaction mixture by any suitable means, for example, it may be precipitated in the presence of a polar organic solvent and subsequently filtered and dried.

Metallocene compounds that can be used in the invention can be obtained commercially or synthesised. One possible chemical synthesis route involves the use of a suitable cyclopentadienide or cyclopentadienide derivative as a starting material. Sodium is reacted with the cyclopentadienide to form sodium cyclopentadienide. Subsequently, a solution containing the transition metal M, for example a solution of the halide salt of the transition metal, is added to sodium cyclopentadienide. The cyclopentadienide reacts with the metal to produce the desired metallocene. (cf. March's Advanced Organic Chemistry, 5$^{th}$ Edition, page 803). Substituted metallocenes which are 'asymmetrical', meaning metallocenes which have two different Cp ligands, can alternatively be obtained by reacting equimolar quantities of 2 different cyclopentadienides, for example. A further possibility of obtaining such asymmetrical metallocenes is to use an unsubstituted metallocene as a starting material. The unsubstituted metallocene can be reacted with a suitable alkyl halide via Friedel Crafts alkylation (requiring the presence of a Brönsted acid e.g. $H_3PO_4$) to obtain both mono- or N,N'-dialkyl substituted metallocenes in the product mixture, the former being the asymmetrical metallocene. Each metallocene can be separated with via any separation technique such as distillation or flash chromatography. Metallocenes suitable in the present invention can also be obtained as described in GB 767,298 and GB 896,391, for example.

If it is desired to obtain a metallocene containing 2 or 3 substituents in one or both of the Cp rings, standard chemical synthesis procedures that are known from the literature can be followed. For example, when $R_b$ is a vinyl group and it is desired to obtain a metallocene in which the substituent $R_a$ is directed to the α position with respect to $R_b$, i.e. a metallocene having a 1,2-substituted Cp ring according to formula IIA, it is possible to follow the synthesis route described in Organic Letters 4 (2002) 707, Tetrahedron: Asymmetry 3 (1992) 753–758 or the respective references cited therein, for instance. Starting from metallocene derivatives as described in these two references that carry carbonyl substituents, compounds of the present invention may be obtained by converting the carbonyl functionality into a C=C double bond by methods known in the art. For example, the aldehyde or ketone may be reacted with a phosphorane or alkyl halide to form a vinyl group via the Wittig reaction, thereby obtaining a vinyl metallocene. If it is desired to obtain a metallocene in which the substituent $R_a$ is directed to the β position with respect to $R_b$, i.e. a metallocene having a 1,3-substituted Cp ring according to formula IIB, it is possible to follow the synthesis route described in Organometallics 19 (2000) 3874–3878, J. Organom. Chem. 598 (2000) 365–373 or the references cited therein, for instance. Alternatively, it might also be possible to use for the generation of compounds of the invention having one or two 1,3-substituted Cp ring(s) any commercially available vinyl-ferrocene as a starting material. The vinyl ferrocene can be alkylated using a suitable alkyl halide via Friedel-Crafts alkylation, for example. The desired metallocene thus produced can be separated from the other concurrently produced by-products via any suitable separation technique, e.g. distillation or chromatography.

Diamines that are suitable for use in the process may also be obtained commercially or can be synthesised through known chemical synthesis routes. For example, a two step process consisting of diamination and alkylation can be used. One example of a known diamination route is the addition of two azido groups to a double bond by treatment with sodium azide ($NaN_3$) and iodosobenzene (PhIO) in acetic acid to form a primary diamine. Another example of a diamination route is the dimerization of imines to give secondary 1,2-diamines. Once the primary or secondary diamine has been formed, it can be converted into the desired tertiary diamine having the structure of formula (IV) via alkylation with an alkyl halide. (cf. March's Advanced Organic Chemistry, $5^{th}$ Edition, page 1056–1057).

In one preferred embodiment, synthesis is carried out in the presence of a polar organic solvent, as it has been found that the presence of a polar organic solvent facilitates the reaction. Examples of suitable polar organic solvents which can be used include short or long chained, branched or unbranched, linear or cylic, aliphatic or aromatic alcohols (e.g. ethanol, propanol, iso-propanol, butanol, pentanol, cyclopentanol, hexanol, cyclohexanol), ketones (e.g. acetone, cyclohexanone, 2,3-butanedione, 1,3-hexanedione, 4-heptanone), aldehydes (e.g. butaraldehyde, 2-ethylhexanal, isobutyraldehyde, isovaleraldehyde, pentanal, phenylacetyldehyde,p-tolualdehyde) carboxylic acids, ethers, and amines.

The compound of the present invention can be synthesised chemically or electrochemically, depending on whether a chemical oxidising agent is used or an electrochemical oxidation potential that is provided by a voltage source is used.

In principle, every known chemical oxidising agent (molecule or compound) may be used in the chemical synthesis of compounds of formula (I), as long as it provides a suitable oxidation potential. Examples of such oxidising agents include, but are not limited to, $H_2CrO_4$, $CrO_3$, $KMnO_4$, $Na_2S_2O_8$, $Cl_2$, $Br_2$, $I_2$, $HNO_3$, $HNO_2$, $SO_3$, $OsO_4$, $NaIO_4$, $NaBrO_4$, $NaClO_4$, and $AgO_2$. In case of the synthesis of ferrocene compounds, a presently preferred oxidising agent comprises persulfate as it provides a suitable oxidising strength to carry out the reaction. Examples of persulfate salts include ammonium persulfate, potassium persulfate and sodium persulfate.

The compound can be synthesised chemically according to the following general procedure. Stoichiometric quantities of the required metallocene are first dissolved in a suitable solvent, for example, a polar organic solvent or a aqueous mixture containing such an organic solvent. Then, a diamine according to formula (IV) is added to the solution. Alternatively, it is also possible to first dissolve the diamine in the solvent prior to adding the required metallocene or its derivative. Finally, the oxidising agent is added to initiate the oxidation of the metallocene, thereby forming a compound of the invention.

The length of time that is required for carrying out the reaction may depend upon several factors, such as temperature, the quantity of reactants added to the reaction mixture, etc. Typically, the reaction is carried out for a period of time between 1 to 30 hours, though longer or shorter reaction times may also be used.

In addition to the chemical synthesis method, it is also possible to synthesise a compound of the present invention via an electrochemical route. In one embodiment, the reaction is carried out in the presence of a support electrolyte. In this case, the oxidising agent is a voltage potential provided by an electrical source. In the electrochemical method, the voltage potential may be provided is various ways, such as by contacting the reaction mixture with an electrode that is coupled to the positive pole of a DC voltage source. Any type of suitable support electrolyte may be used, such as HCl, $KBrO_4$, $NaClO_4$. Tetrabutylammonium hexafluorophosphate is a preferred support electrolyte in the present invention.

In one embodiment, once the compound of the invention is formed, it may be precipitated in a precipitating agent. The precipitating agent can be any suitable polar organic solvent as described above, such as acetone or acetaldehyde. The precipitating agent can be added directly to the reaction mixture in order to precipitate the product. Alternatively, it is also possible to add the reaction mixture dropwise to the precipitating agent.

A further aspect of the invention is directed to the uses of the compound of formula (I). It has been found that the compounds of the inventions can be used in a widespread range of various applications such as biosensing and medical care devices, as catalysts in pollution control, in the oxidative synthesis of organic materials, as tool in molecular biology research or the diagnosis or treatment of diseases such as cancer or any type of tumor.

Amongst the various compounds of the present invention, the ferrocene derivatives have particularly advantageous characteristics that can be harnessed for use in biochemical and catalytic applications. Advantageous properties of ferrocene derivatives which make them suitable for these applications include their water solubility, cationic, stability under ambient conditions, and a redox potential of 200 to 600 mV relative to an Ag/AgCl electrode. Metallocenes have important applications in diverse applications such as electronics, pharmaceuticals, adhesives and tapes. Ferrocenes, nickelocenes and cobaltocenes, for example, are involved in applications such as polyolefin catalysis, biosensing, thermotropic liquid crystals and non-linear optics, diodes, thin film transistors and malarial drugs.

In one presently preferred embodiment, the invention is directed to the use of metallocene compounds of formula (I) as nucleic acid intercalating agent. As illustrated in the examples below such metallocenes exhibit excellent intercalating ability to nucleic acid duplexes. It may be possible that once VFcTMEDA intercalates with the DNA duplex, the base pairs above and below it will 'buckle' in conformation to bring about a distorted DNA helix, thereby preventing association with enzymes such as DNA helicase, DNA topoisomerase and polymerase families of enzymes that initiate DNA replication for RNA synthesis and protein formation, thus halting cell reproduction. For the purpose of tumour treatment, ferrocene compounds of the invention can be administered by any suitable route, for example, orally, intravenously, or subcutaneously. The anti-tumour activity of ferrocene compounds in general is reported in Polyhedron 23 (2004) 823–829; FASEB Journal express article 10.1096/fj.02-0558fje; J. Med. Chem. 2002, 45, 5786–5796; Inorganica Chimica Acta 306(2000) 42–48; and J. Organom. Chem. 418(1991)107–112, for example. Accordingly, the invention is also directed to a pharmaceutical composition containing a compound of formula (I), as well as the therapeutic uses of such a compound.

In addition to the above described biochemical application, ferrocene compounds of the invention can also be used as catalysts. A preferred use is the catalytic oxidation of amines. Catalytic oxidation of amines is widely employed in waste water treatment and the removal of volatile organic compounds (VOCs), hazardous air pollutants (HAPs) and odours from industrial exhaust gas flows. Both applications are required in a large number of industries. Ferrocene compounds of the invention show catalytic activity towards the oxidation of primary, secondary or tertiary amines. In the case of VOC treatment, ferrocene compounds of the present invention can be used traditional two or three-stage odour scrubbing processes. For example, ferrocene derivatives of the invention can be directly included in the scrubbing liquor (typically consisting of dilute sulphuric acid) used in the first stage scrubbing process to remove ammonia and various amines. When used in water treatment, the ferrocene compounds can be directly mixed into primary, secondary, and intermediate treatment plants, and then subsequently precipitated and removed via sedimentation or filtration and then recycled.

EXAMPLES

In the following synthesis examples, electrochemical tests were performed with an Autolab potentiostat/galvanostat running under the general purpose electrochemical system (GPES) manager version 4.9. A conventional three-electrode cell, consisting of an Ag/AgCl reference electrode, a platinum wire counter electrode and a glassy carbon working electrode (surface area of 7.9 mm$^2$) was employed in voltammetric experiments. Controlled-potential coulometry and preparative controlled potential electrolysis were performed in a two-chamber electrochemical cell. The working electrode used in the electrolysis was an assembly consisting of three gold-coated silicon wafers of 1.5×2.0 cm$^2$. A non-leak Ag/AgCl electrode was used as the reference electrode (Cypress Systems, Lawrence, Kans.). The working and reference electrodes were placed in one chamber and the counter was in the other.

Example 1

Electrochemical Synthesis of a High Oxidation State Ferrocene Derivative, VFcTMEDA Sodium persulfate salt and vinylferrocene were purchased from Sigma-Aldrich (St. Luis, Mo., USA.). Tetramethylethylenediamine (TMEDA) was obtained from Avocado Research Chemicals (Heysham, Lancashire, LA3 2XY UK). The weak acid ion-exchange resin used in column chromatographic separation was Amberlite® IRC-50 (16-50 mesh, Sigma-Aldrich). All other chemicals used were of certified analytical grade and all solutions were prepared with deionized water.

In a typical procedure, 20 ml of 0.10 M VFc and 0.50 M TMEDA in acetone containing 0.10 M TBAPF$_6$ as supporting electrolyte was electrolyzed at 0.40 V. Rapid mass transport was sustained in the entire electrolysis period through vigorous N$_2$ purging. To prevent from building up of product on the electrode surface due to its low solubility, leading to electrode fouling and passivation, the cell was placed in an ultrasonic bath. After the current had dropped to less that 2% of the initial value, the electrolysis was considered as terminated. The solvent of the electrolyzed solution was evaporated under reduced pressure. An aliquot of 5.0 ml water was added to the solidified residue. Insoluble material was filtered off. The solute was added to a 50 ml of rapidly stirred acetone to precipitate the compound. Primary purification was done by multiple water dissolving-acetone precipitating cycles. The compound was further purified by column chromatography over the Amberlite® IRC-50 weak acid ion-exchange resin using a 5.0 mM HCl as the eluent. The eluting process was monitored electrochemically, starting to collect the eluent when voltammetric tests showed redox activities at 0.55 V, and the eluting process was considered to be completed when the voltammetric peak currents dropped by more than 80%, as compared to the highest values. The eluent was then neutralized with a 5.0% ammonia solution and evaporated under reduced pressure to near dryness. Ammonium chloride was removed through repetitive washing with an acetone/water mixture. The purified solid obtained was then dissolved in 5.0 ml water and precipitated by slowly adding 30 ml acetone under stirring. The purified product was dried under vacuum at 50° C. overnight.

Example 2

Chemical Synthesis of a High Oxidation State Ferrocene Derivative, VFcTMEDA

The VFcTMEDA compound can also be chemically synthesized as follows. Experimental reagents were obtained as mentioned in Example 1 and tests were carried out with experimental equipment as mentioned therein.

0.20 g of vinylferrocene and 0.60 g TBAPF$_6$ were dissolved in a 10 ml of acetone/water (3/1) mixture. Then 1.00–2.00 ml of TMEDA was added. To initiate the oxidation of vinylferrocene, a 1.0 ml aliquot of 0.50 g/ml oxygen-free persulfate solution was added to the reaction mixture after 10 min of deoxygenating. The reaction mixture was refluxed for 6 h under nitrogen. After cooling, the reaction mixture was added drop-by-drop to 200 ml of rapidly stirred acetone to precipitate the compound. The precipitate was washed with acetone and purified by multiple water-dissolving acetone-precipitating cycles. Further purification was carried out with the column chromatography, as detailed above. The purified product was then dried under vacuum at 50° C. overnight. A typical yield achieved in the present synthesis method was 40–60%.

Example 3

Electrochemical Synthesis of a High Oxidation State Ferrocene Derivative, VFc-Tetramethylpropylenediamine (TMPDA)

Persulfate salt and vinylferrocene were purchased from Sigma-Aldrich (St. Luis, Mo., USA.). Tetramethylpropylenediamine (TMPDA) was from Avocado Research Chemicals (Heysham, Lancashire, LA3 2XY UK). The weak acid ion-exchange resin used in column chromatographic separation was Amberlite® IRC-50 (16-50 mesh, Sigma-Aldrich). All other chemicals used were of certified analytical grade and all solutions were prepared with deionized water.

In a typical procedure, 20 ml of 0.10 M VFc and 0.50 M TMPDA in acetone containing 0.10 M $TBAPF_6$ as supporting electrolyte was electrolyzed at 0.40 V. Rapid mass transport was sustained in the entire electrolysis period through vigorous $N_2$ purging. To prevent from building up of product on the electrode surface due to its low solubility, leading to electrode fouling and passivation, the cell was placed in an ultrasonic bath. After the current had dropped to less that 2% of the initial value, the electrolysis was considered as terminated. The solvent of the electrolyzed solution was evaporated under reduced pressure. An aliquot of 5.0 ml water was added to the solidified residue. Insoluble material was filtered off. The solute was added to a 50 ml of rapidly stirred acetone to precipitate the compound. Primary purification was done by multiple water dissolving-acetone precipitating cycles. The compound was further purified by column chromatography over the Amberlite® IRC-50 weak acid ion-exchange resin using a 5.0 mM HCl as the eluent. The eluting process was monitored electrochemically, starting to collect the eluent when voltammetric tests showed redox activities at 0.55 V, and the eluting process was considered to be completed when the voltammetric peak currents dropped by more than 80%, as compared to the highest values. The eluent was then neutralized with a 5.0% ammonia solution and evaporated under reduced pressure to near dryness. Ammonium chloride was removed through repetitive washing with an acetone/water mixture. The purified solid obtained was then dissolved in 5.0 ml water and precipitated by slowly adding 30 ml acetone under stirring. The purified product was dried under vacuum at 50° C. overnight.

Example 4

Chemical Synthesis of a High Oxidation State Ferrocene Derivative, VFcTMPDA

The VFcTMPDA compound can also be chemically synthesized as follows. Experimental reagents were obtained as mentioned in Example 3 and tests were carried out with experimental equipment as mentioned therein.

0.20 g of vinylferrocene or its derivatives and 0.60 g $TBAPF_6$ were dissolved in a 10 ml of acetone/water (3/1) mixture. Then 1.00–2.00 ml of TMPDA was added. To initiate the oxidation of vinylferrocene, a 1.0 ml aliquot of 0.50 g/ml oxygen-free persulfate solution was added to the reaction mixture after 10 min of deoxygenating. The reaction mixture was refluxed for 6 h under nitrogen. After cooling, the reaction mixture was added drop-by-drop to a 200 ml of rapidly stirred acetone to precipitate the compound. The precipitate was washed with acetone and purified by multiple water-dissolving acetone-precipitating cycles. Further purification was carried out with the column chromatography, as detailed above. The purified product was then dried under vacuum at 50° C. overnight. A typical yield achieved in the present synthesis method was 40–60%.

Example 5

Figure 3:
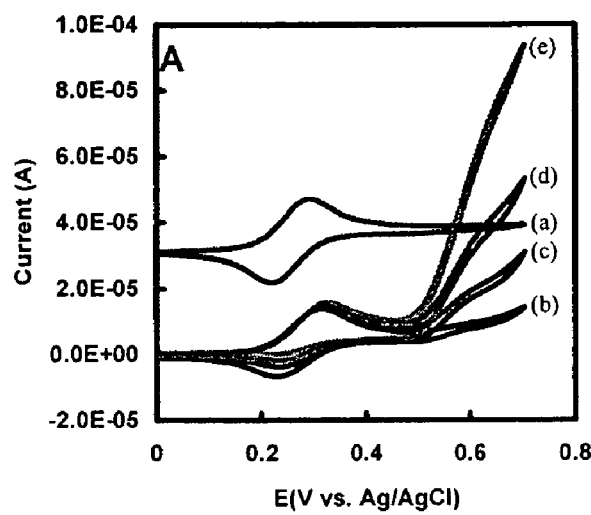
FIG. 3 is a cyclic voltammogram of Vinylferrocene (VFc) in the presence of TMEDA at concentrations of (a) 0 M (b) 0.050 M (c) 0.10 M (d) 0.20 M and (e) 0.30 M.

Cyclic Voltammogram Analysis of VFcTMEDA and VFcTMPDA 20 ml of 0.10 M VFc was placed in vials containing 1 ml of TMEDA at various concentrations of namely 0 M, 0.050 M, 0.10 M, 0.20 M and 0.30 M. To initiate oxidation of vinylferrocene, a 1.0 ml aliquot of 0.50 g/ml oxygen-free persulfate solution was added to the reaction mixture after 10 min of deoxygenating. Cyclic voltammograms of the 5 mixtures were obtained, as shown in FIG. 3.

The first voltammogram (a) at 0.25 V, which has been assigned to the $VFc/VFc^+$ redox couple, has all the characteristics of a reversible process, except the slightly larger peak-to-peak potential separation (65–70 mV), which is mainly due to a higher iR drop of the system. However, the cathodic current $i_c$ of this redox couple decreased significantly compared to the anodic current $i_a$ ($i_c/i_a$=0.30), and lost its reversible characteristics in the presence of 0.10 M TMEDA. Upon increasing the concentration of TMEDA, a typical electrochemically reversible but chemically totally irreversible process (EC) was observed. These changes suggest that the oxidation product, $VFc^+$, once formed, reacts promptly with TMEDA, thereby reducing the concentration of $VFc^+$ at the electrode surface. There was no obvious change in the $i_c/i_a$ ratio when the scan rate was varied from 2 to 2000 mV/s, implying that the reaction between $VFc^+$ and TMEDA is very fast on the electrochemical time scale. The practically 'zero' value of $i_c/i_a$ for the $VFc/VFc^+$ couple observed at higher TMEDA concentration is consistent with a fast and complete follow-up chemical reaction. Scanning to more positive potential revealed that the oxidation current of the second process increased with the increasing concentration of TMEDA. However, the shape of this voltammetric wave remained sinusoidal.

Figure 4:
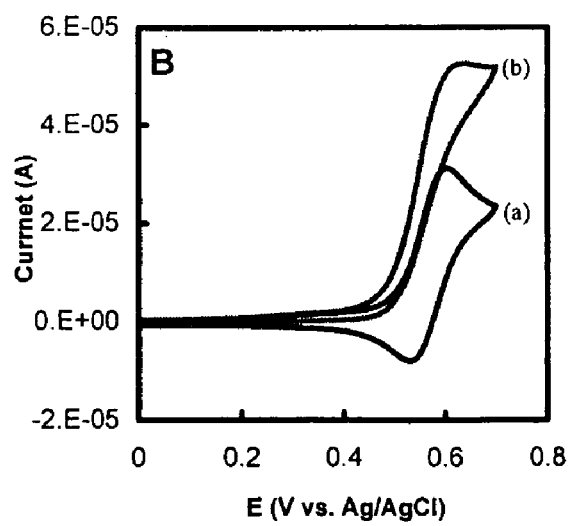
FIG. 4 shows the cyclic voltammogram of VFcTMEDA in the presence of TMEDA at concentrations of (a) 0 M and (b) 5 mM.
Figure 13:
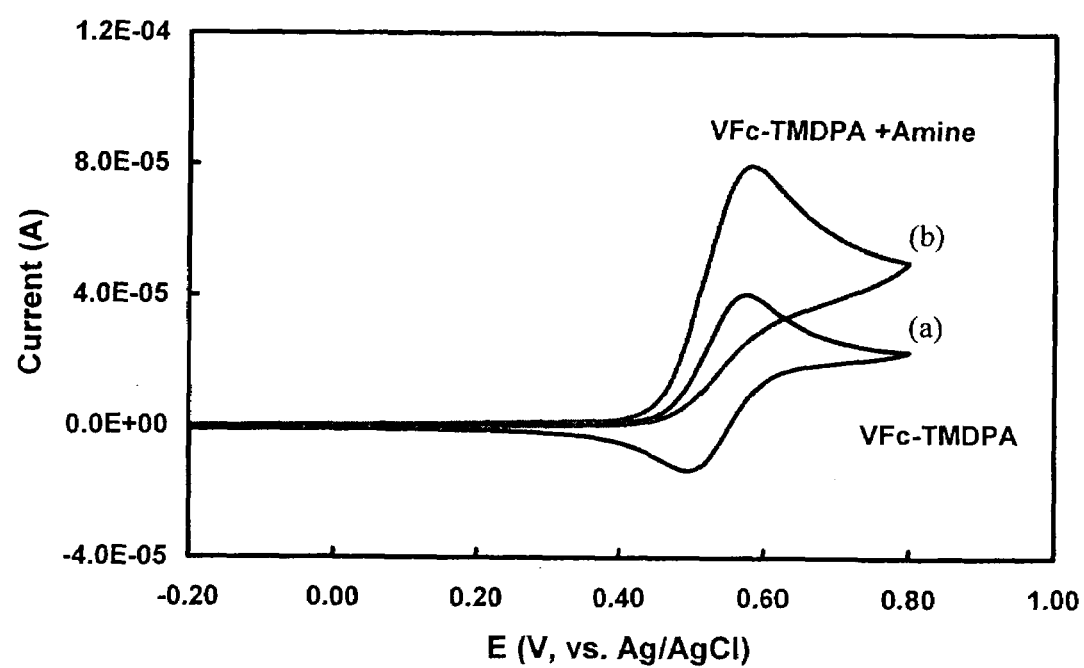
FIG. 13 shows the cyclic voltammograms of a) VFcTMPDA and b) the catalytic oxidation of amine by VFcTMPDA in PBS.

In addition, a tiny amount of brown oily substance was found at the bottom of the electrochemical cell every time after the test. It was solidified and isolated from the reaction mixture with the addition of copious amount of acetone. Unlike vinylferrocene, the brown solid readily dissolved in water. Electrochemical tests indicated that some of the constituents in it exhibited highly reversible redox behaviour at the potential corresponding to that of the second redox process. Removal of the electrochemically inactive constituents and evaporation of the solvent resulted in the crystallization of VFcTMEDA and VFcTMPDA as characterised below. These are the only true $Fc^+$ salt that exhibits the reversible Fe(III)/Fe(IV) transition in aqueous solution under ambient conditions. As shown in FIG. 4 and 13, cyclic voltammetric test clearly showed a couple of highly reversible current peaks with a redox potential coincided well with the second redox process of VFc in the presence of amines, such as TMEDA. Furthermore, the addition of a small amount of TMEDA to the solution resulted in a substantial increase in the oxidation current, a decrease in the reduction current of VFcTMEDA and a typically sinusoidal voltammogram was observed, while no oxidation current was observed when the experiment was conducted in the absence of VFcTMEDA, indicating that a fast electrocatalytic oxidation of the TMEDA by the high oxidation state Fe(IV) of the compound. Amongst the primary, secondary and tertiary amines tested, all of them can be electro-catalytically oxidized by VFcTMEDA or VFcTMPDA.

Example 6

Characterisation of VFcTMEDA and VFcTMPDA

Figure 5:
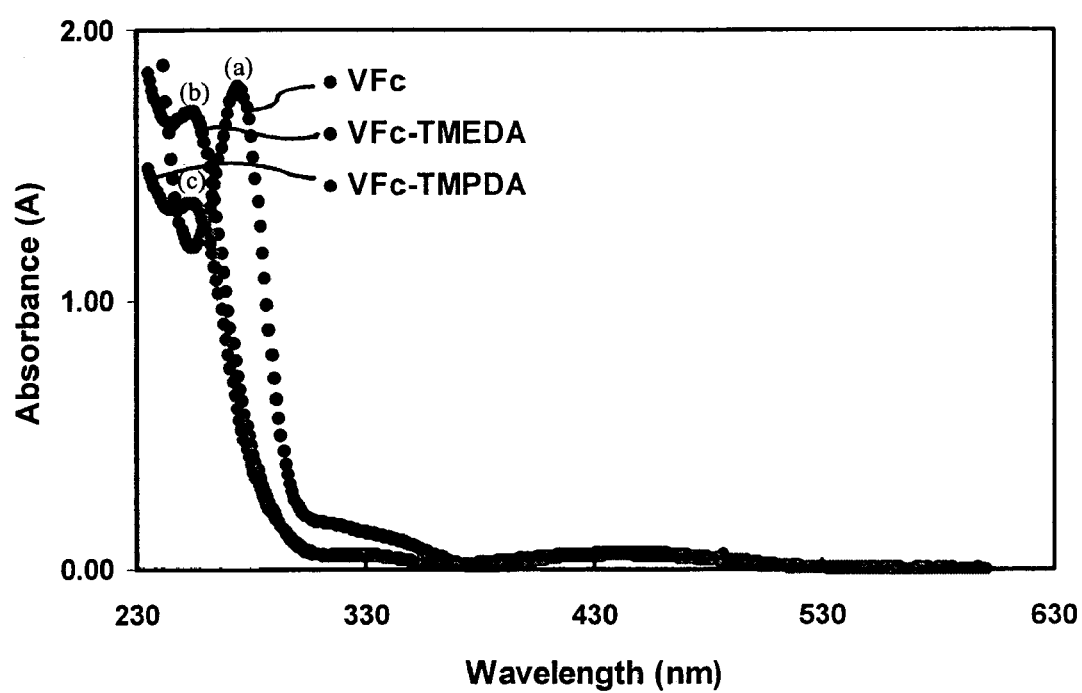
FIG. 5 shows the UV-Visible spectra of (a) VFc (b) VFcTMEDA and (c) VFcTMPDA.

UV spectra of the VFc, VFcTMEDA and VFcTMPDA were obtained using an Agilent 8453 UV-visible spectrophotometer. The UV spectra are depicted in FIG. 5. A blue shift of 25 nm was observed with both VFcTMEDA and VFcTMPDA, which reflects that the electronic π-conjugation is disrupted in the VFc moiety, as a result of the removal of one electron from iron centre in VFc.

Figure 6:
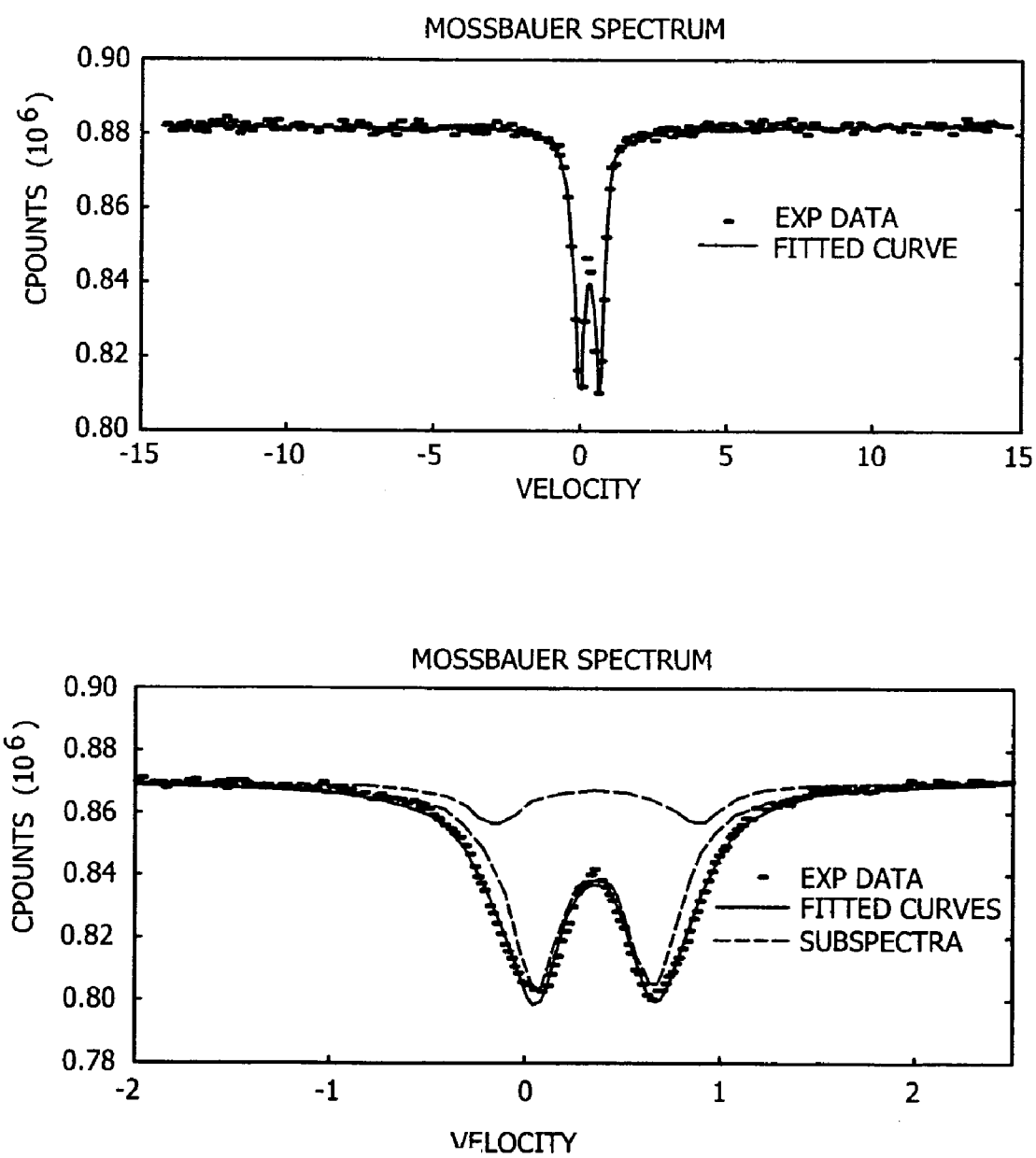
FIG. 6 shows the Mössbauer spectra of VFcTMEDA.

Mössbauer spectroscopic analysis was conducted on an ES-Technology MS 105 Spectrometer with a 25 mCi Co source in a rhodium matrix. Spectra were recorded against an iron foil at 298 K. FIG. 6 shows Mössbauer spectra that was obtained for VFcTMEDA. The Mössbauer parameters for the quadruple splitting $\Delta Eq=0.62$ mm/s and the isomer shift, $\delta=0.30$ mm/s are typical of low spin ferric species. Generally, $\Delta Eq$ of ~0.50 mm/s and $\delta$ of ~2.20 mm/s were obtained for ferrocene derivatives.

Figure 7A:
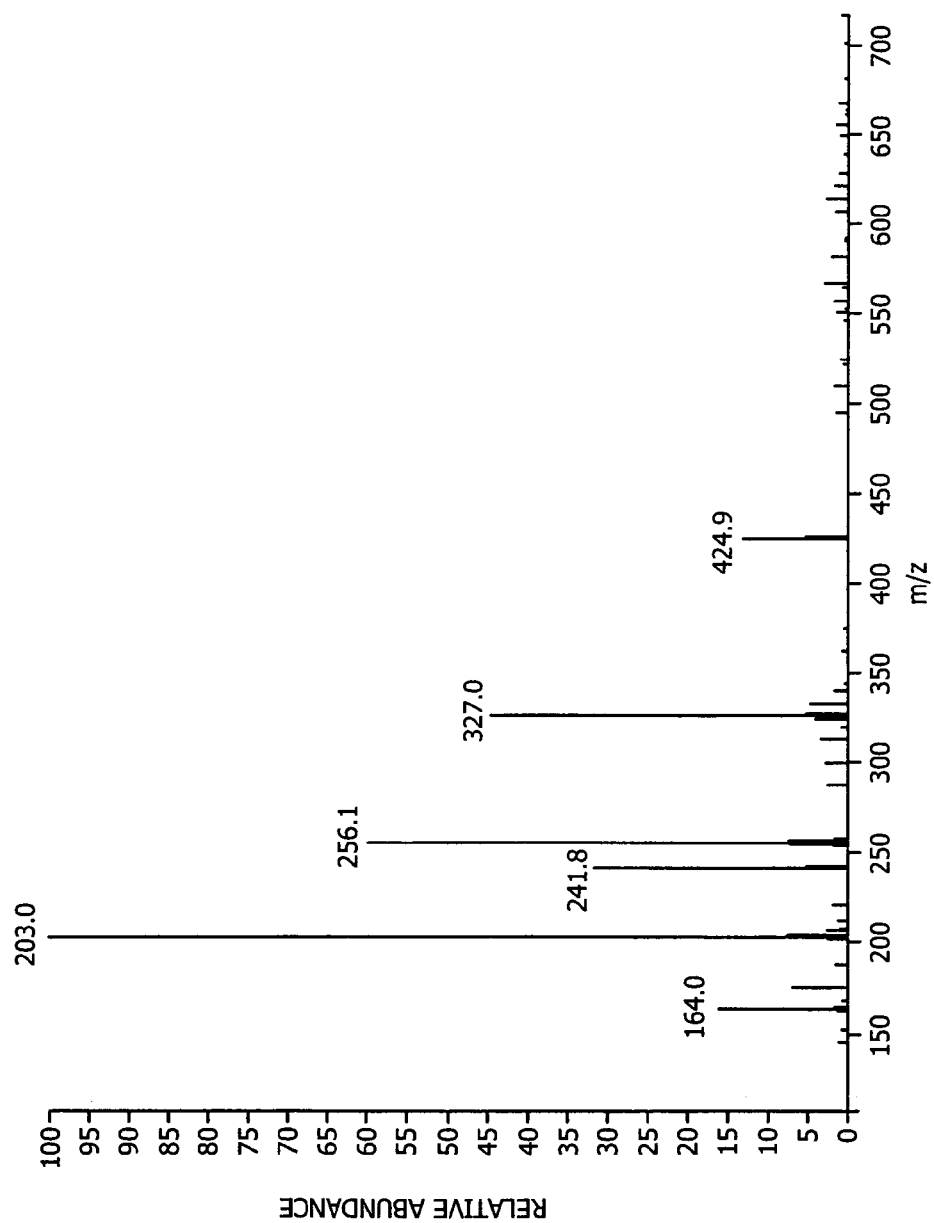
FIGS. 7A and 7B shows the mass spectrum of VFcTMEDA and VFcTMPDA respectively.

Molecular weight of the VFcTMEDA was determined with a Finnigan/MAT LCQ Mass Spectrometer (ThermoFinnigan, San Jose, Calif.). FIG. 7A depicts an electron spray ionization mass spectrum of VFcTMEDA. As often observed in the cases of ferrocene derivatives, the VFc dimer showed much higher relative intensity at 425 (M+1) although it is a by product of an unsuccessful polymerization in minute amount (<5%) in VFcTMEDA. This is probably due to its much higher stability. The molecular mass of VFcTMEDA was found to be at m/z 328, following by a very high intensity at m/z 327 (M−1). It is believed that the compound can easily lose a hydrogen radical at the methylene group adjacent to the vinylferrocene group. Other major primary fragment ions at m/z 256, $[VFc-N(CH_3)_2]^+$, may be produced by the fragmentation of molecular ion at the amine nitrogen coordinated to the $VFc^+$.

Figure 7B:
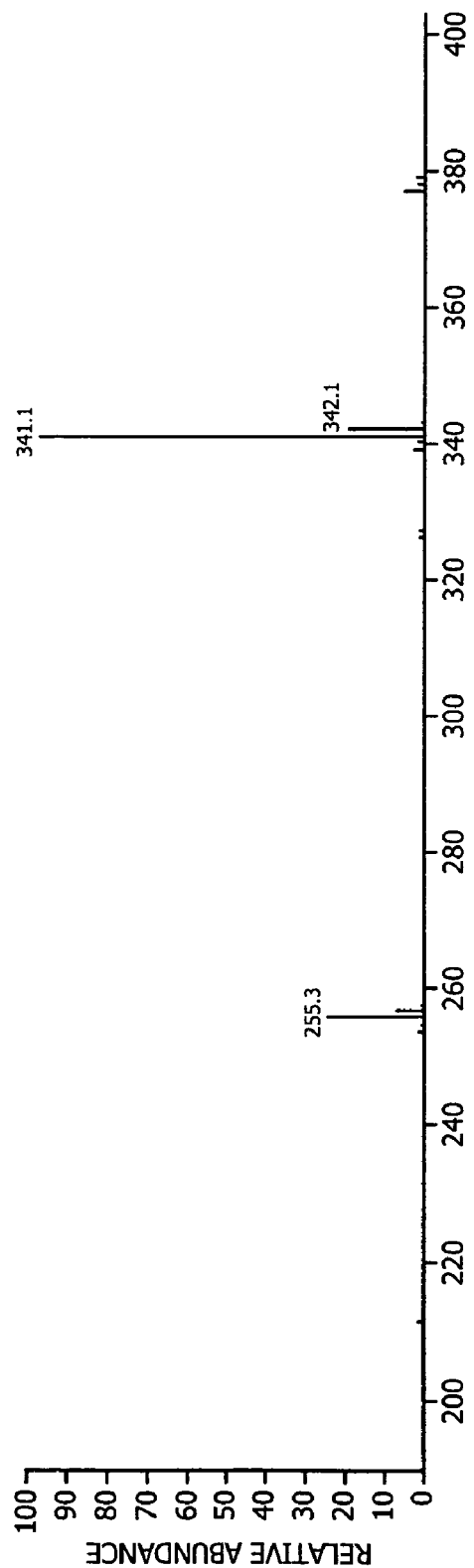

The molecular weight of VFcTMPDA was also determined by mass spectrometry. FIG. 7B depicts the electron spray ionization mass spectrum. The molecular mass of VFcTMPDA is found to be at m/z 342. This result is in agreement with the MS spectra for VFcTMEDA, as VFcTMPDA differs from VFcTMEDA by a $—CH_2—$ moiety, and is thus 14 molecular weight units higher. Similarly, a very high peak was seen at one unit less than molecular mass (M) at m/z 341. A third peak was observed at m/z 255, which is possibly also attributable to the fragmentation of molecular ion at the amine nitrogen coordinated to the $VFc^+$.

Figure 1B:
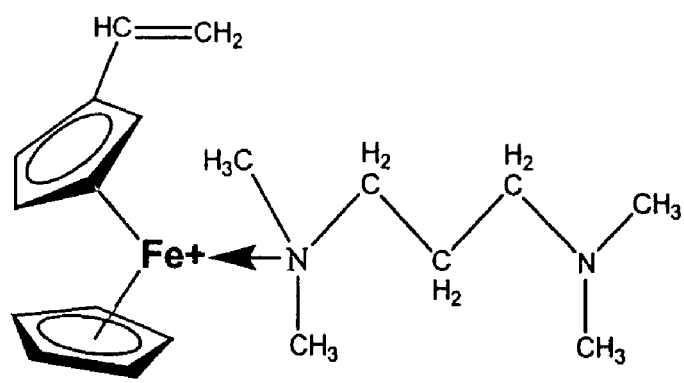
Figure 2:
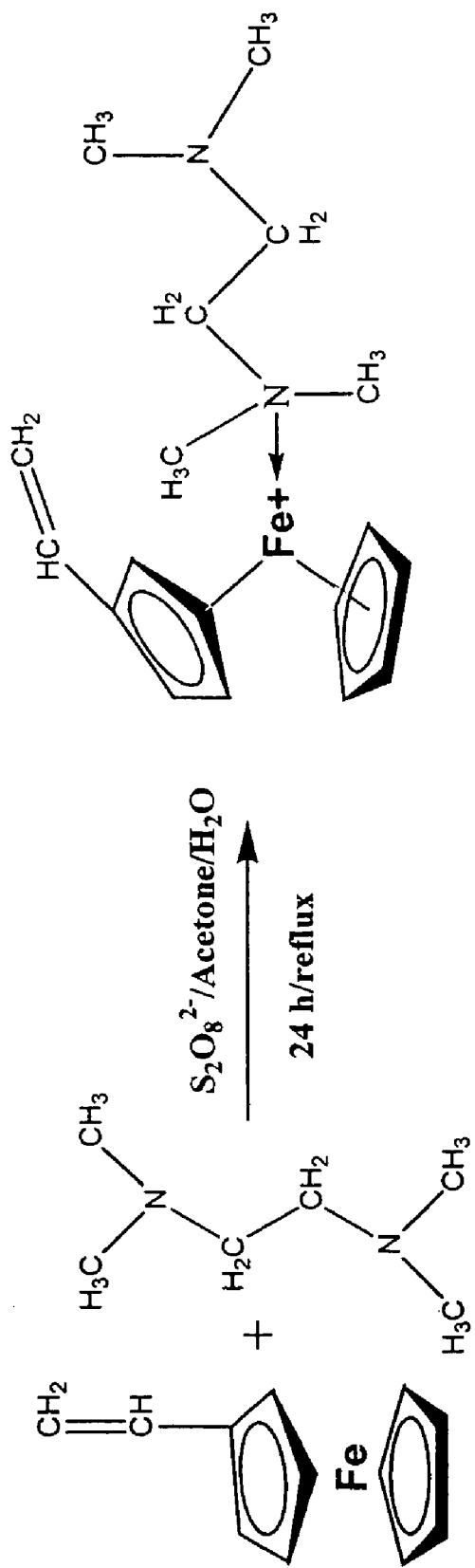
FIG. 2 depicts the reaction equation for producing VFcTMEDA.
Figure 8A:
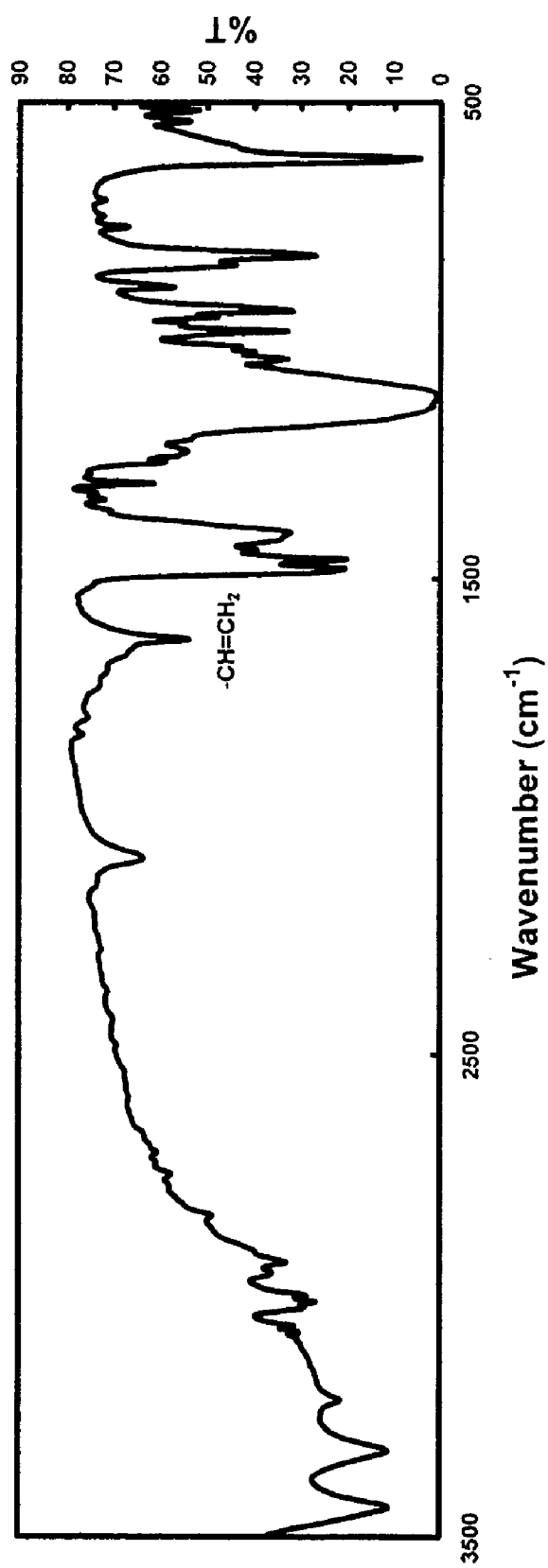
FIGS. 8A and FIG. 8B shows the FT-IR spectrum of VFcTMEDA and VFcTMPDA respectively.
Figure 8B:
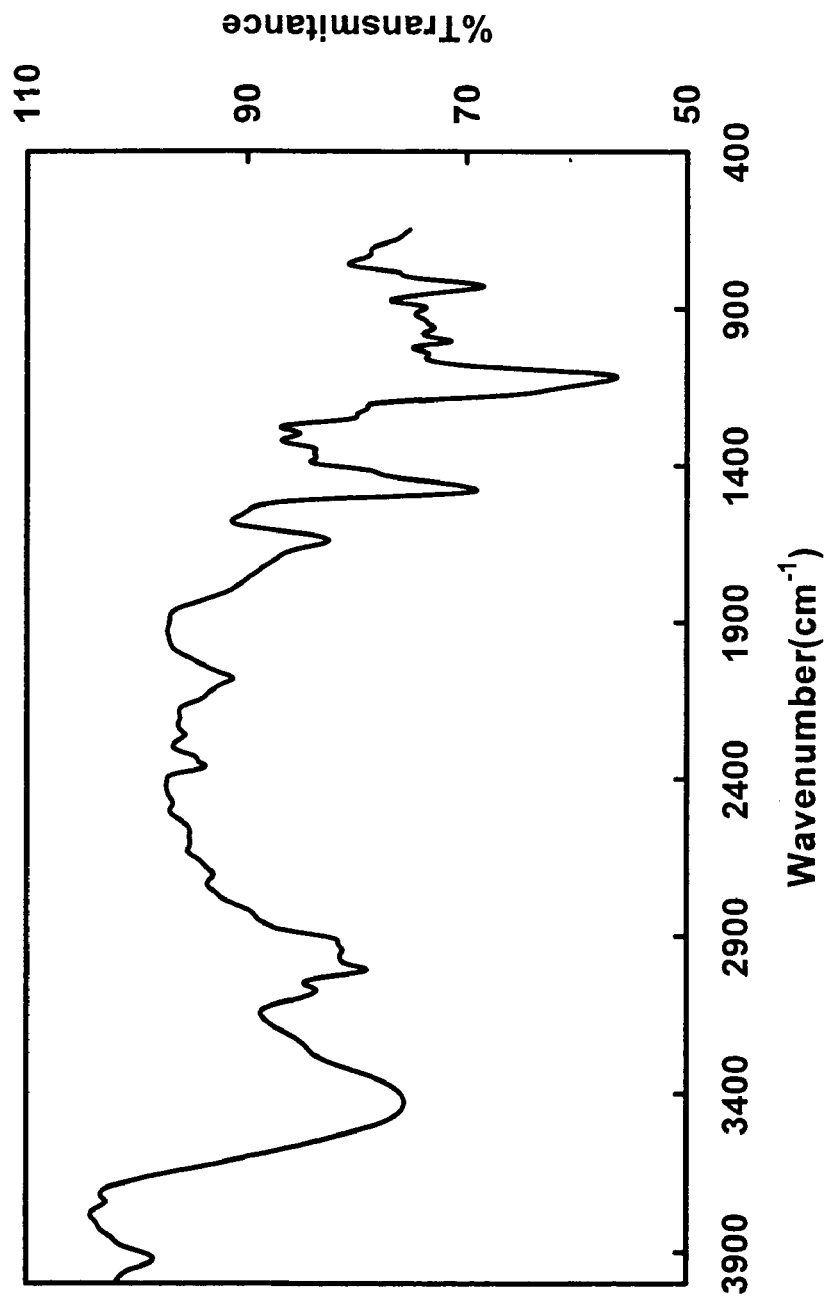

FT-IR spectra were recorded as KBr pellets with a Perkin Elmer Spectrum 2000 FT-IR Spectrometer at a resolution of 4 $cm^{-1}$. All spectra were recorded at room temperature unless otherwise noted. FT-IR spectroscopic studies (FIGS. 8A and 8B) further confirmed that (i) true chemical reaction between VFc and TMEDA/TMPDA reaction has occurred when the oxidative treatment was applied, (ii) vinyl groups on the VFc has been preserved, (iii) little radical coupling between VFc molecules has occurred and (iv) the TMEDA/TMPDA has reacted with $VFc^+$ and a stable compound, as illustrated in FIGS. 1A and 1B, has been produced. It is worth noting that the strong adsorption at 1630 $cm^{-1}$, which is attributed to the vinyl group on one of the cyclopentadienyl rings of VFc. This is a good indication that the complete preservation of the vinyl groups. Supporting evidence can be found in the 1500–1200 and 700–600 $cm^{-1}$ regions. Additionally, the spectrum shows that the cyclopentadienyl rings are stable during oxidative treatment, as evidenced by the strong adsorptions at 3330 and 1140 $cm^{-1}$.

Figure 9A:
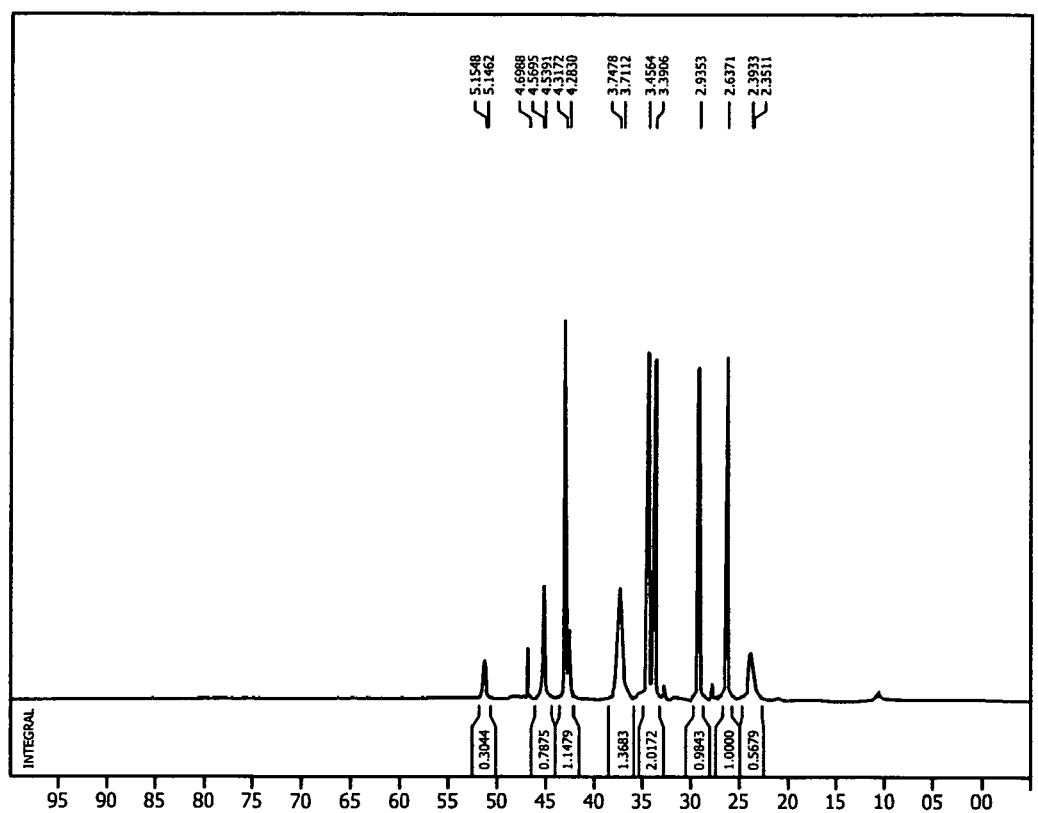
FIG. 9A and FIG. 9B show the NMR spectra of VFcTMEDA and VFcTMPDA respectively.

NMR spectra were recorded using a Bruker ACF3000 spectrometer operating at 300 MHz. Evidence of the formation of VFcTMEDA was also provided by $^1H$ NMR spectrum and 2-D carbon-hydrogen heteronuclear correlated NMR spectrum, as shown in FIG. 9A. As can be seen in the figure, the $^1H$ NMR spectrum and the 2-D $^{13}C$-$^1H$ correlated spectrum are complimentary to each other, nine chemical shifts of hydrogen atoms were obtained between 0 and 6.0 ppm and 12 chemical shifts of carbon atoms were observed which are consistent with the proposed chemical structure. Analysis of these spectra independently confirmed the formation of VFcTMEDA.

Example 7

Use of VFcTMEDA as an Intercalating Agent

In initial experiments it was found that the compounds of the inventions have DNA intercalating properties. A competition experiment was designed to obtain an estimate of the nucleic acid intercalating property of the compound of the invention. The basis of this methodology involves the use of two intercalators, one fluorescent and one non-fluorescent. The fluorescent intercalator first saturates the double-stranded DNA. Then a second intercalator, in this case VFcTMEDA, is introduced into the system with gradual increasing concentration. It was thought that two molecules would bind to similar sites in the double-stranded DNA. For the competition experiment, the changes in fluorescent intensity were monitored during the displacement of DNA-bound fluorescent molecules by VFcTMEDA through an increasing concentration of the VFcTMEDA molecules in the system. A well-known threading intercalator, ethidium bromide (EB), was chosen as our fluorescent indicator. EB has been widely studied as an efficient DNA intercalator and is one of the most popular fluorescent intercalators used in nucleic acid assay. EB displays a 25-fold fluorescence enhancement upon binding to the double-stranded DNA, which provides sufficient sensitivity and good discrimination against free EB molecules in fluorescent measurement. In addition, the kinetics of EB intercalation is quite fast, which significantly shortens the time needed to reach equilibrium.

Figure 9B:
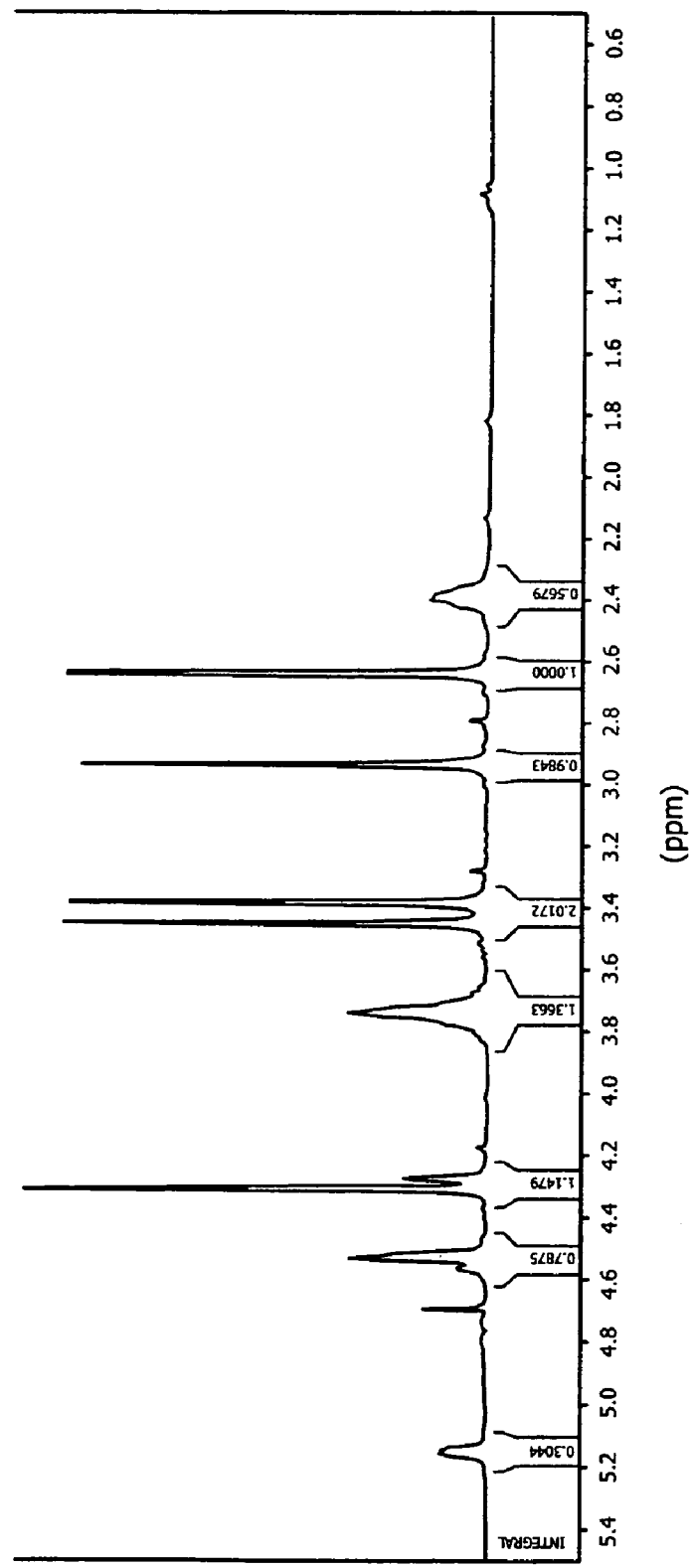

To ensure that this approach is appropriate, an increasing concentration (0–100 μM) of a well-studied non-fluorescent intercalator, naphthalene diimide (ND) was first added to the EB saturated double-stranded DNA solution, gel electrophoresis experiment showed that the fluorescent intensity of the EB intercalated DNA diminished gradually as the concentration of ND increased. The binding constant $K_d$ of $4.0\times10^5$, estimated from the experimental data, was in good agreement with literature value. Subsequently, VFcTMEDA was studied with respect to its ability to compete against EB for binding to DNA using the same approach. Different amounts of VFcTMEDA were mixed with the EB saturated double-stranded DNA to examine the bind ability. As shown in FIG. 9, VFcTMEDA exhibited a remarkable binding affinity towards the double-stranded DNA. Lanes 1 to 5 correspond to different ratios of VFcTMEDA/EB. The higher the ratio of VFcTMEDA/EB, the lower the fluorescent intensity. The lower fluorescent intensities of the DNA obtained with the higher ratios of VFcTMEDA/EB (lanes 3–5) suggested that more VFcTMEDA molecules are bound to the double-stranded DNA and larger amounts of EB molecules are replaced. As shown by the second lane, at a VFcTMEDA/EB molecular ratio of as low as 1/5, more than 50% of the DNA-bound EB was replaced, suggesting that VFcTMEDA is a much stronger DNA intercalator than EB. The binding constant $K_d$, estimated from the experimental data, was $4.4 \times 10^6$, corresponding to approximately a 26-fold enhancement over EB. However, a closer examination of the gel image showed that accompanying the weakening of fluorescent intensity, there was a systematic change in DNA mobility. The higher the ratio of VFcTMEDA/EB, the higher the band appeared in the gel image, and in turn, the slower the mobility of the DNA. The molecular mass of ethidium bromide is 324 and that of VFcTMEDA is 328, as determined by MS spectrometry. Both of them are mono-cationic. Therefore, the less than 2% mass difference between EB and VFcTMEDA is ruled out for causing such a big mobility change. A plausible explanation is that VFcTMEDA intercalates more sites on DNA than EB. At low VFcTMEDA/EB ratios, VFcTMEDA preferably intercalates with DNA at free sites and then replaces EB as its concentration increases. This implies that the $K_d$ value of $4.4 \times 10^6$ obtained is smaller than its true value.

Example 8

Use of VFcTMEDA in the Catalytic Oxidation of Amines

Figure 10:
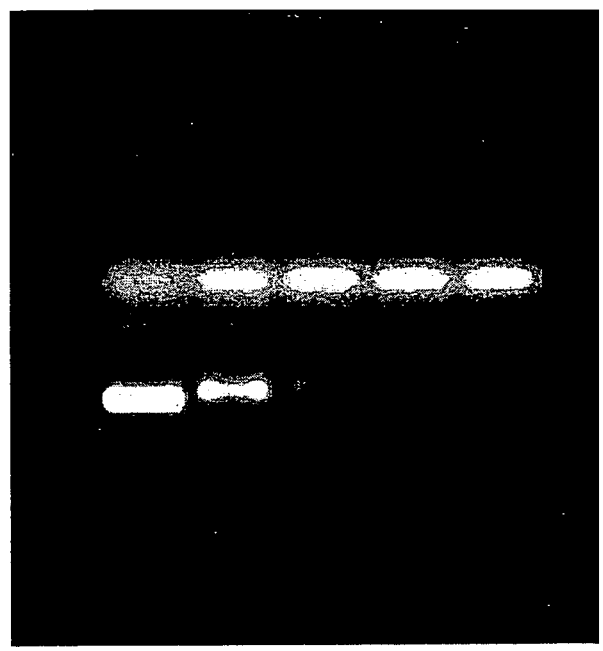
FIG. 10 illustrates the DNA binding property of VFcTMEDA. The ratio of VFcTMEDA to ethidium bromide (EB), from the left to the right, is 0/1, 1/5, 1/2, 1/1 and 2/1.
Figure 11:
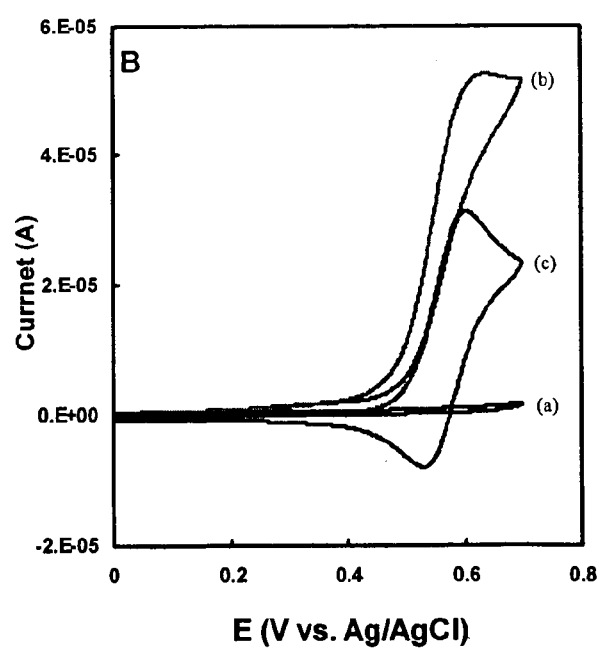
FIG. 11 shows the cyclic voltammogram for the oxidation of 5.0 mM TMEDA in the presence of VFcTMEDA at concentrations of (a) 0 M (b) 0.50 mM. PBS is present in both samples. The cyclic voltammogram for VFcTMEDA in PBS is shown in (c).

Voltammograms of amines in solution containing 0.0 M and 5.0 mM VFcTMEDA at a glassy carbon electrode is shown in FIG. 10, taking TMEDA as an example. For comparison, a voltammogram of the VFcTMEDA in PBS was also presented in FIG. 10. In a pure TMEDA solution, no oxidation current was observed between 0.0 and 0.70 V indicating that TMEDA cannot be oxidized at potentials less positive than 0.70 V. In fact, electrochemical oxidations of amines in PBS only take place at potentials beyond 0.90 V. It can be seen that in the presence of VFcTMEDA, the overpotential of TMEDA oxidation was reduced substantially, shifting the peak potential negatively by as much as 400 mV, to 0.60 V. Meanwhile the reduction peak of VFcTMEDA significantly diminished, suggesting that an efficient catalytic reaction between VFcTMEDA and TMEDA occurs in the solution. Similar catalytic effects on other amines oxidations were also observed, regardless primary, secondary or tertiary.

Figure 12:
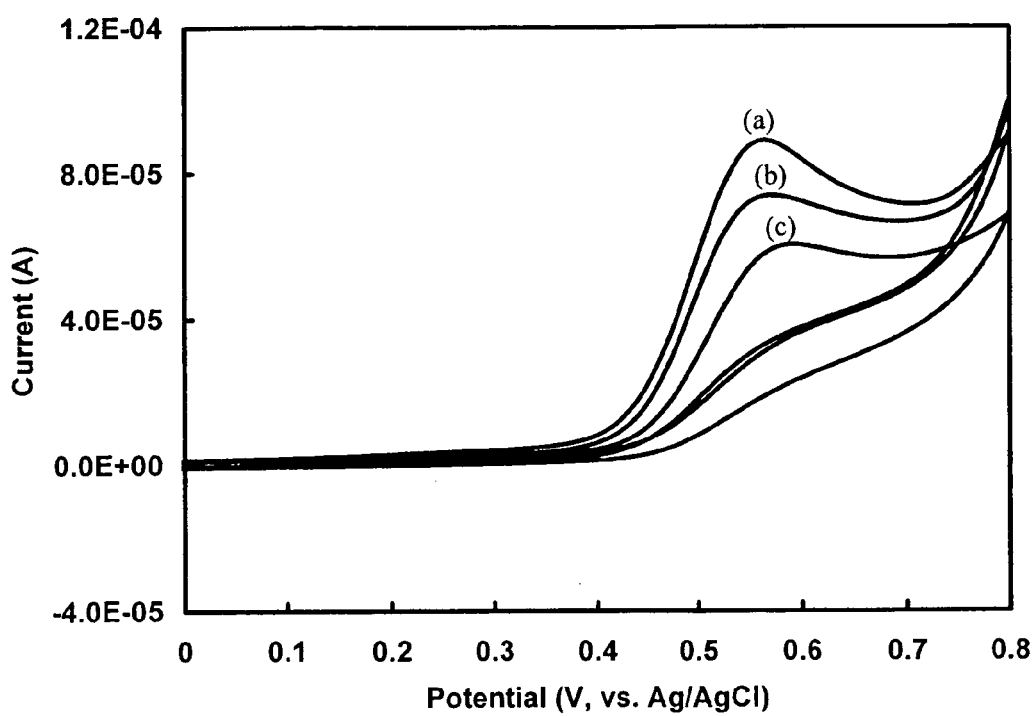
FIG. 12 shows the cyclic voltammogram for the oxidation of 5.0 mM of (a) $NH_3$, (b) $C_2H_5NH_2$ and (c) $CH_3$—NH—$C_2H_5$, all in PBS and in the presence of VFcTMEDA at a concentration of 0.5 mM.

The catalytic oxidation of other amines was also carried out with VFcTMEDA. FIG. 12 shows cyclic voltammograms of 5.0 mM (a) $NH_3$, (b) $C_2H_5NH_2$ and (c) $CH_3$—NH—$C_2H_5$, all in solutions containing the same amounts of PBS. VFcTMEDA was present at a concentration of 0.5 mM at a glassy carbon electrode. It can be seen that in the presence of VFcTMEDA, the peak potential of the oxidation of ammonia was at about 0.58V, same as the case for $C_2H_5NH_2$. For $CH_3$—NH—$C_2H_5$, the peak potential was at about 0.59V. In the presence of VFcTMEDA, all three oxidation potentials are much less than the commonly known oxidation potential in PBS without VFcTMEDA of over 0.9V for the electrochemical oxidation of amines.

It can be seen from FIG. 13 that the voltammogram response in the oxidation of amines by VFcTMPDA is similar to that of VFcTMEDA, with the peak oxidation potential being about 0.58V and oxidation current of about $8 \times 10^{-5}$ amperes.

It was found that the pH values have a profound effect on the catalytic oxidations of amines. The pH of the electrolyte solution was adjusted by adding aliquots of 0.10 M $Na_3PO_4$ solution to a 10 ml of 0.10 M $H_3PO_4$ solution. Since electrochemical oxidation of VFcTMEDA does not involve proton, its redox potential is pH independent. But to have an efficient catalytic effect, the pH of the medium must be above 7.0, indicating that deprotonation of amines is an essential part of the oxidation process. Consequently, in an acidic medium, the catalytic oxidations of amines were retarded. Furthermore, it was found that upon reacting with dissolved oxygen, the light yellow solution of TMEDA containing 0.20 mg/ml VFcTMEDA changed from pale yellow to deep brown, implying that amines can be oxidized chemically by dissolved oxygen under ambient conditions. This is especially attractive in developing a pollutant removal system for amines, such as ammonia in water.

What is claimed is:

1. A compound having the formula (I):

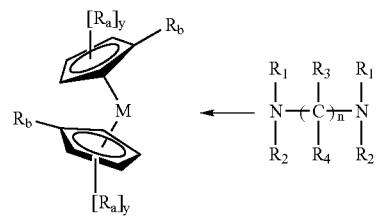

wherein:

M is a transition metal selected from Groups 4 to 10 (IUPAC, 1990);

$R_a$ is H or C1 to C6 alkyl, optionally substituted;

y is an integer of 1 or 2;

$R_b$ is H, or a vinyl group having the formula (II):

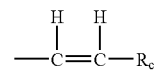

or the formula (IIA):

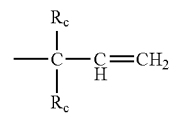

or the formula (IIB):

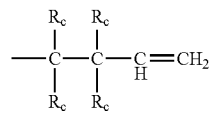

wherein $R_c$ is H or C1 to C6 alkyl, optionally substituted;

$R_1$ and $R_2$ are independently selected from C1 to C6 alkyl, optionally substituted;

$R_3$ and $R_4$ are independently selected from H or C1 to C6 alkyl, optionally substituted; and n is an integer of 2 or 3.

2. The compound of claim 1, having the formula (IA):

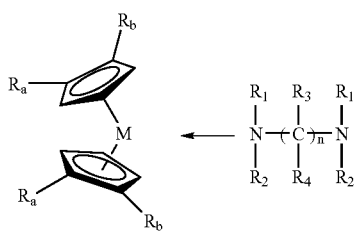

wherein M, $R_a$, $R_b$, $R_1$, $R_2$, $R_3$ and $R_4$ have the same meanings as defined in claim 1.

3. The compound of claim 1, having the formula (IB):

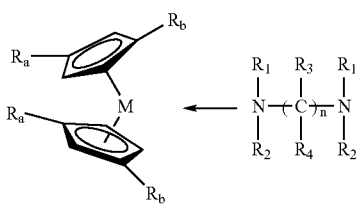

wherein M, $R_a$, $R_b$, $R_1$, $R_2$, $R_3$ and $R_4$ have the same meanings as defined in claim 1.

4. The compound of claim 1, wherein $R_a$ and $R_c$ are each independently selected from the group consisting of hydrogen, methyl, ethyl, propyl, isopropyl, n-propyl, butyl, n-butyl, tert-butyl, pentyl, n-pentyl, iso-pentyl, n-hexyl and iso-hexyl, all optionally substituted.

5. The compound of claim 1, wherein $R_1$ and/or $R_2$ are each independently selected from the group consisting of methyl, ethyl, propyl, isopropyl, n-propyl, butyl, n-butyl, tert-butyl, pentyl, n-pentyl, iso-pentyl, n-hexyl and iso-hexyl, all optionally substituted.

6. The compound of claim 1, wherein $R_3$ and/or $R_4$ are each independently selected from the group consisting of hydrogen atom, methyl, ethyl, propyl, isopropyl, n-propyl, butyl, n-butyl, tert-butyl, pentyl, n-pentyl, iso-pentyl, n-hexyl and iso-hexyl, all optionally substituted.

7. The compound of claim 1, wherein the moiety

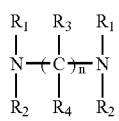

in formula (I) is selected from the group consisting of tetramethyl-1-methyl-ethylenediamine, tetraethyl-ethylenediamine, N,N'-diethyl-N,N'-dimethyl-ethylenediamine, N,N'-dimethyl-N,N'-diethyl-1-methyl-ethylenediamine, tetrapropyl-ethylenediamine, N,N'-dimethyl-N,N'-dipropyl-ethylenediamine, tetramethyl-propylenediamine, tetraethyl-2-ethyl-propylenediamine, N,N'-diethyl-N,N'-dimethyl-propylenediamine, and N,N'-Diisopropyl-N,N'-dimethyl-1,3-propanediamine.

8. The compound of claim 1, wherein M is a metal selected from the group consisting of Fe, Co, Ni, Mn, Zr, Cr, Ti, V, Os, and Ru.

9. The compound of claim 1, wherein the overall charge of the compound is positive.

10. The compound of claim 1, wherein the compound is represented by the formula (VII):

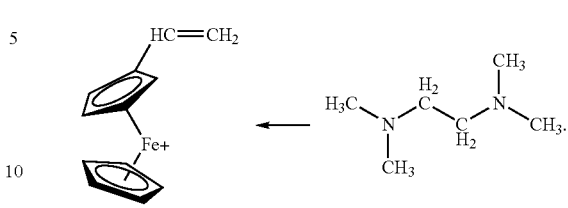

11. The compound of claim 1, wherein the compound is represented by the formula (VIII):

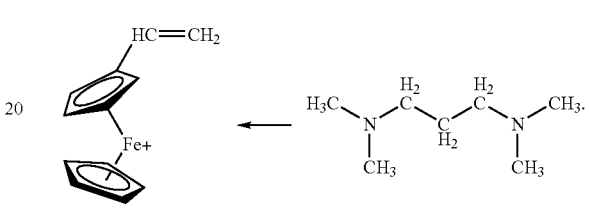

12. A process for preparing an organometallic compound comprising:

reacting a compound having the formula (III):

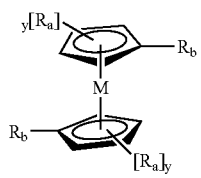

with a compound having the formula (IV):

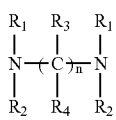

wherein:

M is a transition metal selected from Groups 4 to 10 (IUPAC, 1990);

$R_a$ is H or C1 to C6 alkyl, optionally substituted;

$R_b$ is H, or a vinyl group having the formula (II):

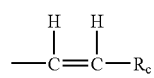

or the formula (IIA):

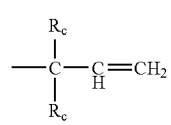

or the formula (IIB):

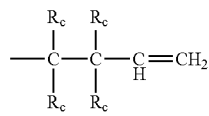

wherein $R_c$ is H or C1 to C6 alkyl, optionally substituted;
$R_1$ and $R_2$ are independently C1 to C6 alkyl, optionally substituted,
$R_3$ and $R_4$ are independently H or $CH_3$, optionally substituted; and
n is an integer of 2 or 3;
said reaction being carried out in the presence of an oxidising agent.

13. The process of claim 12, wherein the reaction mixture comprises a polar organic solvent.

14. The process of claim 12, wherein the oxidising agent comprises a chemical oxidising agent selected from the group consisting of a salt of persulfate, chlorate, bromate, peroxide, or a mixture thereof.

15. The process of claim 12, wherein the reaction is an electrolytic reaction carried out in the presence of a support electrolyte, and wherein the oxidising agent is a voltage potential provided by an electrical source.

16. The process of claim 15, wherein the support electrolyte is tetrabutylammonium hexafluorophosphate.

17. The process of claim 12, further comprising precipitating the product in a precipitating agent.

18. A method of altering a nucleic acid, comprising contacting a nucleic acid with a compound having the formula (I) as defined in claim 1 so that the compound intercalates with the nucleic acid.

19. A method of catalyzing oxidation of an amine, comprising contacting an amine with a compound having the formula (I) as defined in claim 1 to catalyze oxidation of the amine.

* * * * *